(12) United States Patent
Wang et al.

(10) Patent No.: US 11,337,629 B2
(45) Date of Patent: *May 24, 2022

(54) RENAL FUNCTION ANALYSIS METHOD AND APPARATUS

(71) Applicant: PHARMACOPHOTONICS, INC., Indianapolis, IN (US)

(72) Inventors: Exing Wang, Carmel, IN (US); Daniel Meier, Indianapolis, IN (US); Robert Bunch, Terre Haute, IN (US); Bruce Molitoris, Indianapolis, IN (US); Ruben Sandoval, Indianapolis, IN (US); Matthew Rubin, Indianapolis, IN (US)

(73) Assignee: PHARMACOPHOTONICS, INC., Indianapolis, IN (US)

( * ) Notice: Subject to any disclaimer, the term of this patent is extended or adjusted under 35 U.S.C. 154(b) by 255 days.

This patent is subject to a terminal disclaimer.

(21) Appl. No.: 16/692,490

(22) Filed: Nov. 22, 2019

(65) Prior Publication Data
US 2020/0100720 A1    Apr. 2, 2020

Related U.S. Application Data

(63) Continuation of application No. 15/218,417, filed on Jul. 25, 2016, now Pat. No. 10,485,469, which is a (Continued)

(51) Int. Cl.
*A61B 5/1455* (2006.01)
*A61B 5/20* (2006.01)
(Continued)

(52) U.S. Cl.
CPC .......... *A61B 5/201* (2013.01); *A61B 1/00154* (2013.01); *A61B 1/00165* (2013.01);
(Continued)

(58) Field of Classification Search
CPC ... A61B 5/14546; A61B 5/0474; A61B 5/412; A61B 5/0275; A61B 5/201;
(Continued)

(56) References Cited

U.S. PATENT DOCUMENTS 3,878,830 A    4/1975   Bicher
4,795,434 A    1/1989   Kujawski
(Continued)

FOREIGN PATENT DOCUMENTS

EP    1568333 A    8/2005
EP    1604689 A1   12/2005
(Continued)

OTHER PUBLICATIONS

Ashworth, S. L., et al.,"Two-photon Microscopy: Visualization of Kidney Dynamics", Kidney International 200708 GB, vol. 72, No. 4, Aug. 2007 (Aug. 2007), pp. 416-421.
(Continued)

*Primary Examiner* — Eric F Winakur
(74) *Attorney, Agent, or Firm* — Brannon Sowers & Cracraft PC

(57) ABSTRACT

A method for measuring a glomerular filtration rate in a mammalian kidney comprises a source of reporter and marker fluorescent molecules. The fluorescent molecules are introduced into the blood stream of a mammalian subject. Over a period of time, a measurement of the intensities of the reporter and marker fluorescent molecules is taken. A ratio is calculated to determine the health of the subject's kidney. This method measures volume of plasma distribution based on a fluorescence of a marker molecule relative to a fluorescence of a reporter molecule.

18 Claims, 11 Drawing Sheets

Related U.S. Application Data continuation of application No. 13/713,189, filed on Dec. 13, 2012, now Pat. No. 9,398,876, which is a continuation of application No. 12/425,827, filed on Apr. 17, 2009, now abandoned.

(60) Provisional application No. 61/046,273, filed on Apr. 18, 2008.

(51) Int. Cl.
    *A61B 5/00*         (2006.01)
    *A61K 49/00*      (2006.01)
    *A61B 1/00*         (2006.01)
    *A61M 5/00*       (2006.01)

(52) U.S. Cl.
CPC .......... *A61B 5/0071* (2013.01); *A61B 5/0084* (2013.01); *A61B 5/412* (2013.01); *A61B 5/6852* (2013.01); *A61K 49/0017* (2013.01); *A61M 5/007* (2013.01)

(58) Field of Classification Search
CPC ..... A61B 5/0071; A61B 5/007; A61B 5/0075; A61B 5/0084; A61B 5/6852
See application file for complete search history.

(56) References Cited

U.S. PATENT DOCUMENTS

| | | | |
|---|---|---|---|
| 4,906,232 | A | 3/1990 | Reynolds |
| 5,678,550 | A | 10/1997 | Bassen et al. |
| 5,798,276 | A | 8/1998 | Haugland et al. |
| 5,920,399 | A | 7/1999 | Sandison et al. |
| 5,928,625 | A | 7/1999 | Dorshow et al. |
| 6,036,654 | A | 3/2000 | Quinn et al. |
| 6,280,703 | B1 | 8/2001 | Combs et al. |
| 7,892,203 | B2 | 2/2011 | Lenker et al. |
| 8,591,865 | B2 | 11/2013 | Wang et al. |
| 9,398,876 | B2 | 7/2016 | Wang et al. |
| 2004/0260182 | A1 | 12/2004 | Zuluaga et al. |
| 2005/0020891 | A1 | 1/2005 | Rubinstein et al. |
| 2005/0136002 | A1 | 6/2005 | Fossheim et al. |
| 2017/0014065 | A1 | 1/2017 | Wang et al. |

FOREIGN PATENT DOCUMENTS

| | | |
|---|---|---|
| WO | 199963328 A | 12/1999 |
| WO | 2006113724 | 10/2006 |
| WO | 2006113724 A1 | 10/2006 |
| WO | 2007058616 A | 5/2007 |

OTHER PUBLICATIONS

Molitoris, B. A, et al., "Pharmacophotonics: Utilizing Multi-Photon Microscopy to Quantify Drug Delivery and Intracellular Trafficking in the Kidney", Advanced Drug Delivery Reviews, Elsevier BV, Amsterdam, NL, vol. 58, No. 7, Oct. 31, 2006 (Oct. 31, 2006), pp. 809-823.
"International Search Report for PCT/US2009/040994 dated Dec. 8, 2009".
Sapirstein. et al., Volumes of distribution and clearances of intravenously injected creatinine in the dog*, Ameri can JQyrnal of Phy:§iolog:-r:; vol. 181, No. 2, 1955 oaaes 330-336• XP008115469.
Xue, Jay L. et al., "Incidence and Mortality of Acute Renal Failure In Medicare Beneficiaries, 1992 to 2001", J Am Soc Nephrol 17: 1135A.?1142, 2006. doi: 10.1681/ASN.2005060668 Jan. 15, 2006.
Annet, L., et al., "Glomerular Filtration Rate: Assessment with Dynamic Contrast-Enhanced MRI and a Cortical-Compartment Model in the Rabbit Kidney," J. Magn Reson Imaging, vol. 20, No. 5, 2004, pp. 843-849.
Brewer, B. D., et al., "Single Injection Inulin/PAH Method for the Determination of Renal Clearances in Adult Horses and Ponies," J Vet Pharmacol Ther, vol. 11, No. 4, 1988, pp. 409-412.
Buonocore, M. H., et al., "Estimation of Extraction Fraction (EF) and Glomerular Filtration Rate (GFR) Using MRI: Considerations Derived from a New Gd-Chelate Biodistribution Model Simulation," IEEE Trans Med Imaging, vol. 24, No. 5, 2005, pp. 651-666.
Cousins, C.. et al., "Comparative Kinetics of Microvascular Inulin and 99mTc-Labelled Oiethylenetriaminepenta-acetic Acid Exehange," Clin Sci (Lond), vol. 93, No. !5, 1997, pp. 471-477.
Cousins, C., et al., "Clearance Kinetics of Solutes Used to Measure Glomerular Filtration Rate," Nucl Med Commun, vol. 20, No. 11, 1999, pp. 1047-1054.
Dagher, P. C., et al., "Newly Developed Techniques to Study and Diagnose Acute Renal Failure," J Am Soc Nephrol, vol. 14, No. 8, 2003, pp. 2188-2198.
Filler, G., et al., "Cystatin C as a Marker of GFR—History, Indications, and Future Research," CUn Biochem, vol. 38. No. 1, 2005, pp. 1-8.
Fischer, P. A., et al., "A New Procedure for Evaluation of Renal Function Without Urine Connection in Rat," Kidney Int., vol. 58, No. 3. 2000, pp. 13361341.
Greenblatt. D. J. et al., "Clinical Pharmacokinetics (firat of two Parts)," N. Engl.J. Med., vol. 293, No. 14, 1975, pp. 702-705.
Greenblatt. D. J., et al., "Clinical Phannaeokinetics (second of two Parts)," N. Engl. J. Med., vol. 293, No. 19, 1975, pp. 964-970.
Haller, M., et al., "Single-Injection Inulin Clearance for Routine Measurement of Glomerular Filtration Rate in Cats," J. Feline Med Surg, vol. 5, No. 3, 2003, pp. 175-181.
Lorenz, J. N., et al., "A Simple Nonradioactive Method for Evaluating Single-Nephron Filtration Rate Using FITC-Inulin," Am J Physiol, vol. 276, 1 Pt 2, 1999, pp. F172-F177.
Meucci, V., et al., "A New HPLC Method to Determine Glomerular Filtration Rate and Effective Renal Plasma Flow in Conscious Dogs by Single Intravenous Administration of Iohexol and P-Aminohippurtc Acid," J Chromatogr Sci, vol. 42, No. 2, 2004, pp. 107-111.
Prescott, L. F., et al., "Reassessment of the Single Intravenous Injection Method with Inulin for Measurement of the Glomerular Filtration Rate in Man," Clin Sci (Land), vol. 80, No. 2, 1991, pp. 167-176.
Qi, z., et al., "Serial Determination of Glomerular Filtration Rate in Conscious Mice using FITC-lnulin Clearance," Am J Physiol Renal Physiol, vol. 286, No. 3, 2004, pp. F590-F596.
Rabito, C. A., et al., "Noninvasive, Real-Time Monitoring of Renal Function: The Ambulatory Renal Monitor," J. Nucl Med, vol. 34, No. 2, 1993, pp. 199-207.
Rabito, C. A., et al., Noninvasive, Real-Time Monitoring of Renal Function During Critical Care,* J. Am Soc Nephrol, vol. 4, No. 7, 1994, pp. 1421-1428.
Rusinek, H., et al."Renal Magnetic Resonance Imaging," Curr Opin Nephrol Hypertens, vol. 13, No. 6, 2004, pp. 667-673.
Sapirsteln, L. A., et al., "Valldlty of Values for Glomerular Filtration Rate and Extracellular Fluid Obtained From Plasma Concentration-Time Decay Curves After Single Injections of Mannitol in the Dog," Am J. Physiol, vol. 171, No. 2, 1952, pp. 487-491.
Wholohan, T., et al., "Comparison of a Single-Injection Technique and Inulin Clearance for Determining Glomerular Filtration Rate in the Sheep," Exp Physiol, vol. 76, No. 2, 1991, pp. 289-291.
Examiner Requisition for Canadian Application No. 2,721,846 dated Sep. 7, 2017.
Molitoris, "Intravital multiphoton microscopy of dynamic renal processes", Am J Physiol Renal Physiol., 288/6, pp. F1084-F1089, Jun. 2005.
Sapirstein, "Volumes of distribution and clearances of intravenously injected creatinine in the dog." Am. J. Physiol., 181/2, pp. 330-336, 1955.
Examination Report, dated Mar. 30, 2017, for India Patent Application No. 8116/DELNP/2010, Patent Office India.
Dunn et al.; "Functional studies of the kidney of living animals using multicolor two-photon microscopy" American Journal of Physiology, vol. 283, Sep. 2002, pp. 905-916.
Zhang et al. (Journal of Neuroscience Methods, 1998, vol. 85, pp. 51-62).
Fritzsch (Journal of Neuroscience Methods, 1993, vol. 50, pp. 95-103).

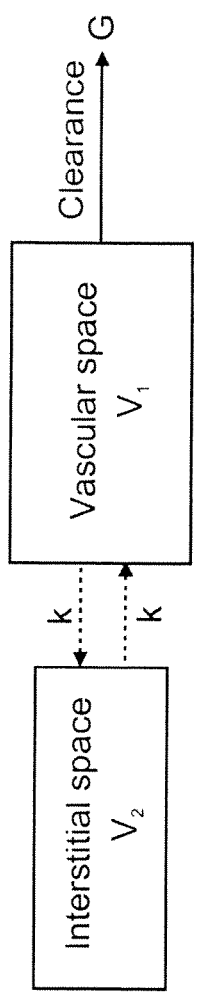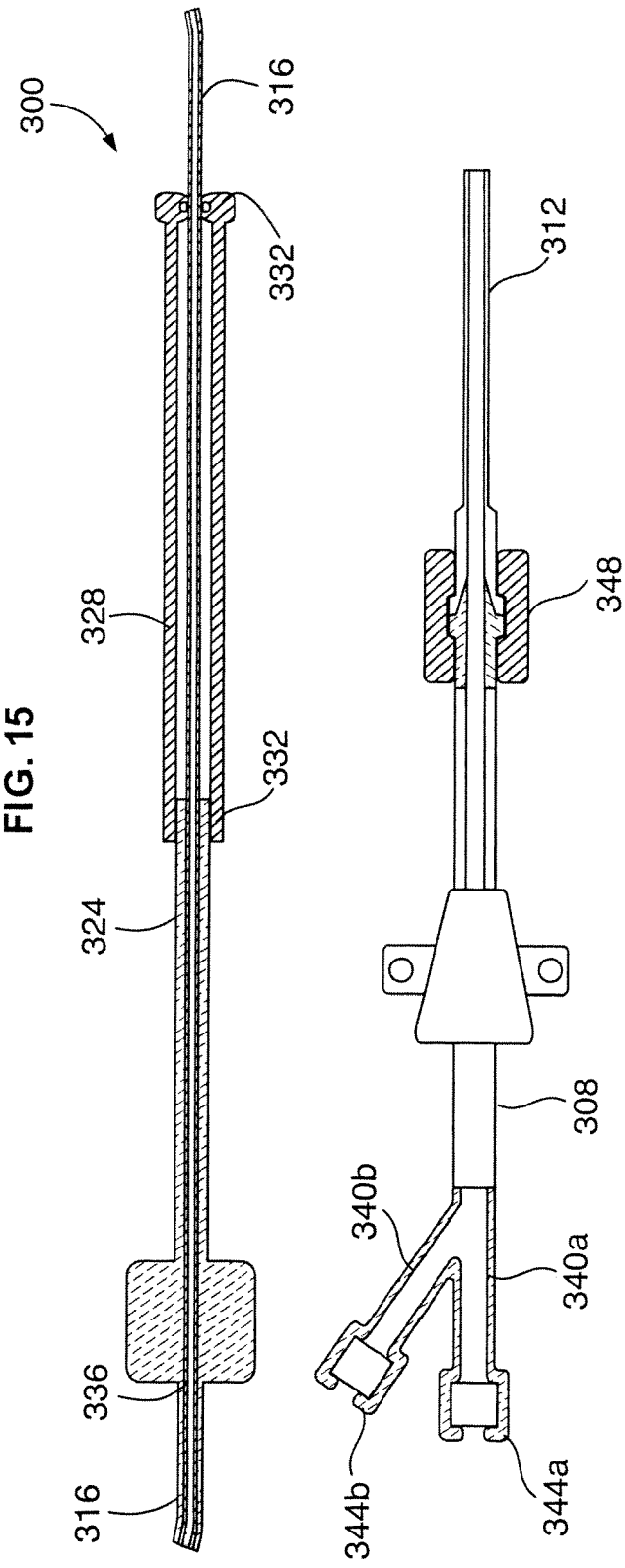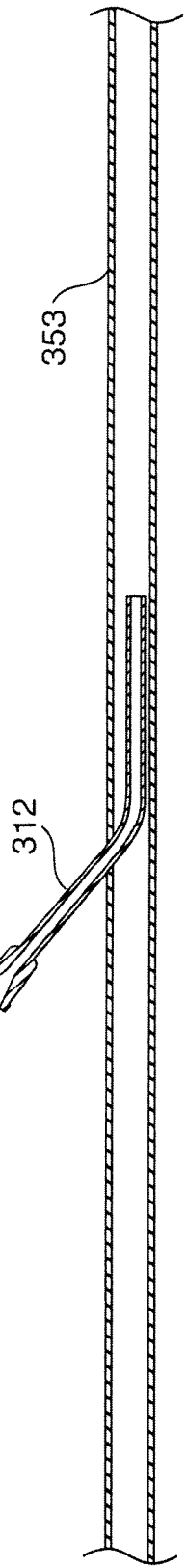
FIG. 15
FIG. 16

RENAL FUNCTION ANALYSIS METHOD AND APPARATUS

CROSS-REFERENCE TO RELATED APPLICATIONS

This application is continuation of U.S. Application Ser. No. 15/218,417, filed on Jul. 25, 2016, which is a continuation of U.S. Application Ser. No. 13/713,189, filed Dec. 13, 2012, which is a continuation of U.S. Application Ser. No. 12/425,827, filed Apr. 17, 2009, which claims priority to U.S. provisional Application No. 61/046,273, filed Apr. 18, 2008, all of which are hereby incorporated herein in their entirety by reference.

FEDERALLY SPONSORED RESEARCH OR DEVELOPMENT

N/A

TECHNICAL FIELD

The invention relates to medical methods and devices used in conjunction with analyzing organ functions. More particularly, the present invention is directed to an apparatus and method used for analyzing and quantifying function of a mammalian kidney.

BACKGROUND OF THE INVENTION

Acute kidney injury (AKI) is a serious and deadly disease process affecting 5-10% of all hospitalized patients. The mortality rate in these cases often exceeds 50%. AKI is independently associated with increased mortality rates in several clinical situations, including subsequent to administration of radio contrast dye and cardiovascular surgery. It is often multi-factorial in etiology, especially in critically ill patients. The relative importance of individual factors depends upon the underlying pathology and patient co-morbidities.

Recent data demonstrate an alarming increase in the total number of cases of AKI. Utilizing patient claims in the Medicare 5% sample from 1992-2001, Xue et al (J Am Soc Nephrol 17:1135-1142 2006) have shown that during this time period, the incidence of AKI increased approximately 11.6% per year from 23.6 cases per 1,000 discharges in 1992 to 63.3 cases per 1,000 patients in 2001.

In a recent study, Hsu et al (Hsu, et al., "Community-Based Incidence of Acute Renal Failure," Kidney Int. 2007; 72(2):208-12.) quantified the incidence of non-dialysis and dialysis AKI among members of a large integrated health care delivery system. Between 1996 and 2003, the incidence of non-dialysis-requiring AKI increased from 323 to 522 while the incidence of dialysis-requiring AKI increased from 20 to 30 per 100,000 person years. Furthermore, hospital death rates were much higher in patients with AKI than in non-AKI discharges. Patients without AKI had a 4.6% in-hospital death rate while those with primary AKI and secondary AKI had rates of 15.2 and 32.6%, respectively. Death within 90 days after hospital admission was 13.1% in discharges without AKI, 34.5% and 48.6% of patients with primary and secondary AKI, respectively. In this large study, the probability of developing end stage renal disease was 18.8% in patients with acute kidney injury as a principle diagnosis and 10.1% in patients with acute renal failure as a secondary diagnostic code. Finally, using the data collected, it was calculated that at least 22.4% of the end stage renal disease (ESRD) cases in the United States come from Medicare beneficiaries who had hospital acquired AKI.

These data are in agreement with observations made by Dr. Paul Eggers, director of epidemiology NIDDK, indicating a rapid increase in the percentage and absolute number of hospitalized patients with AKI as a primary or secondary diagnosis and in patients with chronic kidney disease (CKD) progressing onto ESRD having had AKI as a hospital diagnosis.

In another study (Uchino, et al., "An Assessment of the RIFLE Criteria for Acute Renal Failure in Hospitalized Patients," Crit. Care Med. 2006; 34(7): 1913-7.) the incidence and outcomes of 20,126 hospitalized patients was determined in a retrospective single-center study. Of these patients 14.7% required ICU admission, 18% had AKI, and mortality correlated with the extent of kidney injury. Finally, in a multi-center retrospective ICU study AKI occurred in 67% of admissions and again the overall prognosis correlated with the severity of AKI.

Clearly, the prevalence of AKI in hospitalized patients is increasing at an alarming rate. The severity of injury determines hospital outcomes, and AKI accelerates the development of chronic kidney disease and progression of CKD to ESRD.

It is believed that glomerular filtration rate GFR is the most relevant metric for determining the extent of AKI and progression of CKD. Reductions in the GFR secondary to kidney injury, either acute or chronic, are accompanied by increases in blood urea nitrogen (BUN) and serum creatinine levels. Currently, either serum creatinine or an equation based on the serum creatinine is used to determine a patient's estimated GFR (eGFR). Unfortunately, these two approaches are not reliable over the full range of GFR, and neither can be used in AKI, since both muscle mass (creatinine is a breakdown product of creatine, which is an important part of muscle) and GFR determine a patient's serum creatinine level.

Using serum creatinine as an indicator of GFR is highly patient specific. For instance, a serum creatinine of 1.0 mg/dl is indicative of a normal GFR (100 ml/min) in a 70 Kg (154 lb) male with normal muscle mass. However, in a 50 Kg (110 lb) male with moderate muscle wasting, a serum creatinine of 1.0 mg/dl is seen even though his GFR is only 50 ml/min. Formulas derived from large population studies have been developed to factor in patient weight, age, sex and race. However, even these formulas are inaccurate and often misleading in estimating GFR below 20 or above 60 ml/min. Therefore, this is another reason they cannot be used in the setting of AKI.

Recent data indicate that even very small changes in kidney function, as determined by small total equilibrium elevations in serum creatinine, previously felt to be clinically insignificant, are now known to predict an increased mortality rate. Several recent publications have utilized the Risk, Injury, Failure, Loss and ESRD criteria (often called "RIFLE" criteria) to stratify patients into apparent levels of injury based on the maximum serum creatinine obtained and the need for dialysis. Data collected for mortality, length of hospital stay (LOS), LOS of ICU stay, hospital costs, and the need for renal replacement therapy related to the highest stage achieved in this stratification system. These data indicate that the severity or extent of kidney injury in AKI is an important prognostic indicator of a patient's outcome. Furthermore, early changes in organ function predict survival in severe sepsis.

Serum creatinine determinations as a measure of GFR may also be severely limiting because of the time it takes to reach equilibrium values required for an accurate conversion. Patients with acute renal failure develop an abrupt decline of their GFR; however, the magnitude of this decline is only apparent after several days of equilibration if determined by a rising serum creatinine. For instance, if a patient was to lose 95% of his GFR secondary to AKI, the GFR would decrease from 100 to 5 ml/min rapidly, but the serum creatinine would only rise by 1 mg/dl/day. This slow rise in serum creatinine limits the physician's ability to diagnose the injury for 12-24 hours after the event, and it is also not possible to determine the extent of injury for days. This has markedly limited the ability to conduct a therapeutic trial in AKI. Since the extent of the decline in GFR, or eventual plateau in serum creatinine, correlates with morbidity, mortality and recovery potential, the ability to accurately determine GFR in patients with acute kidney injury is of great clinical importance for rapid diagnosis, stratification and timely treatment.

It is widely held that beginning therapy after 12-24 hours of AKI may limit the success rate of any potential therapeutic agent. Therefore, a search for a biomarker of kidney injury has intensified and is now considered by many experts to be the highest priority in the field of AKI. Potential molecules include NGAL, KIM-1, IL-18, and several others. Any one biomarker, or probably a combination of biomarkers, will serve as structural markers of injury. However, improvements sought utilizing these structural biomarkers may not be significant because they were developed using population results that may not apply to an individual.

Collection of a 24 hour urine and invasive techniques exist to accurately determine a patient's GFR, but these are cumbersome, error prone, expensive, time consuming, or expose the patient to radiation or radio contrast media. Also, there is no rapid and accurate measurement technique that can determine GFR reliably in patients with acute kidney injury when the serum creatinine is rising.

The liver is responsible for several activities including clearing metabolites and toxins from the blood, making bile, lipid metabolism, drug metabolism, metabolizing many medications, storing various vitamins and protein synthesis. Unfortunately, the liver may be diseased either acutely or chronically and its ability to perform various vital functions may be limited. In an intensive care unit, one of the liver's most important functions is to metabolize medications, either from their inactive to their active state or vice versa. As a result, liver health may be critical to determining how much medication should be introduced into a patient and for how long. Current methods of quantifying and/or detecting liver function or dysfunction are generally vague and qualitative and may include jaundice, darkened urine, nausea, loss of appetite, unusual weight loss or weight gain, vomiting, diarrhea, light colored stools, generalized itching, hypoglycemia, and the like. Unfortunately, these tools of detecting liver health are often identical to signs used to detect other major health issue and are often useless when diagnosing and treating a patient with multiple morbidities. As a result, many liver diseases remain unrecognized until they reach a severe state where metabolic functions and ascites are often more definitive signs. As a result, a more quantitative rather than qualitative diagnostic for liver function is needed.

The present invention is provided to solve the problems discussed above and other problems, and to provide advantages and aspects not provided by prior diagnostic techniques. A full discussion of the features and advantages of the present invention is deferred to the following detailed description, which proceeds with reference to the accompanying drawings.

SUMMARY OF THE INVENTION

One aspect of the present invention is directed to a composition for introduction into a mammalian subject's vascular system to analyze an organ function. The composition comprises a reporter molecule and a marker molecule. The reporter molecule and the marker molecule share a common molecular property. The reporter molecule has a reporter molecule molecular property of a first quality, and the marker molecule has a marker molecule molecular property of a second quality which is distinguishable from the reporter molecule molecular property first quality. The molecular property may be chosen from the group consisting of molecular weight, molecular size, molecular shape, molecular charge, compound, and radio frequency.

When the molecular property is molecular weight, the reporter molecule may have a first molecular weight and the marker molecule may have a second molecular weight. The first molecular weight may be less than the second molecular weight, and may be substantially less. The first molecular weight may be of a magnitude wherein the reporter molecule is filtered by a properly functioning mammalian kidney. The second molecular weight may be great enough to resist filtration of the marker molecule by a mammalian kidney. Optionally, the first molecular weight may be of a magnitude wherein the reporter molecule is readily filtered by a properly functioning mammalian kidney, while at the same time, the second molecular weight is great enough to resist filtration of the marker molecule by a mammalian kidney. The first molecular weight may be chosen from a group of ranges consisting of 1 kD to 500 kD, 3 kD to 150 kD, 10 kD to 150 kD, 10 kD to 70 kD, and 20 kD to 70 kD. Alternatively, the first molecular weight may be less than 500 kD, between 1 kD and 500 kD, 3 kD and 150 kD, between 3 kD and 70 kD, between 3 kD and 20 kD, or about 5 kD.

The reporter molecule may have a first fluorescent characteristic, and the marker molecule may have a second fluorescent characteristic. These fluorescent characteristics may not be equal, e.g. having differing wavelengths. The first fluorescent characteristic may be a first fluorescence excitation wavelength and a first fluorescence emission wavelength. The second fluorescent characteristic may be a second fluorescence excitation wavelength and a second fluorescence emission wavelength. The first and second fluorescence excitation wavelengths and the first and second fluorescence emission wavelengths may be different, unequal, or distinguishable.

The reporter and marker molecules may be dextrans. The reporter molecule may be a sulphorhodamine 101 dextran. The marker molecule may be a larger undefined dextran that is not filtered by a mammalian kidney. The reporter molecule and the marker molecule may be dextrans conjugated with fluorescein. Additionally, the reporter molecule fluorescein may have a fluorescence excitation wavelength that is not equal to a fluorescence excitation wavelength of the marker molecule.

Alternatively, the reporter molecule and the marker molecule may be dextrans conjugated with different fluorophores. Additionally, the fluorescent reporter molecule may have a fluorescence excitation wavelength that is not equal to a fluorescence excitation wavelength of the marker molecule.

The reporter molecule may be a fluorescein isothiocyanate-inulin.

The marker molecule may have a glomerular sieving coefficient of about 0.

The marker molecule may not be not secreted, reabsorbed, or filtered by a mammalian kidney.

The marker molecule may not be capable of passing through a glomerular filtration barrier, and the reporter molecule may be capable of passing through a glomerular filtration barrier.

A second aspect of the present invention is directed to an apparatus for analyzing an operating condition of a mammalian kidney. The apparatus comprises a source of fluorescent molecules, a means for introducing the fluorescent molecules into a vascular system, a means for measuring the fluorescent molecules within the vascular system, and a means for reporting the measured fluorescent molecules within the vascular system. The means for introducing may include a catheter. The means for measuring may include an optic fiber in communication with a detector. The means for reporting may include determining an intensity ratio between two or more fluorescent molecules measured within the vascular system. The source of fluorescent molecules may comprise a plurality of fluorescently conjugated molecules.

A third aspect of the present invention is directed to an apparatus for analyzing an operating condition of a mammalian kidney. The apparatus comprises an optical means providing a first excitation wavelength to a first fluorescent molecule and a means for measuring an emission from the first fluorescent molecule in response to the first excitation wavelength.

The optical means may emit a second excitation wavelength to a second fluorescent molecule, and the apparatus may further comprise a means for measuring an emission from the second fluorescent molecule in response to the second excitation wavelength.

The apparatus of the third aspect of the invention may further comprise a means for calculating a ratio of the emission from the first fluorescent molecule to the emission from the second fluorescent molecule. The apparatus may still further comprise a means for reporting the ratio.

A fourth aspect of the present invention is directed to an optical apparatus for measuring a relative amount of a plurality of fluorescently conjugated glomerular filtration rate molecules within a vascular system. The apparatus comprises a source of a first fluorescent excitation wavelength, a delivery optical path along which the fluorescent excitation wavelength passes, an excitation site to which the fluorescent excitation wavelength is delivered, a return optical path along which an emitted fluorescence signal passes, and a means for detecting an intensity of the emitted fluorescence signal. This apparatus may further comprise a source of a second fluorescence excitation wavelength.

The means for detecting may be chosen from a group consisting of a photo multiplier tube, a photo detector, a solid state detector, and a charge-coupled device.

The excitation site may include a fiber optic cable.

A fifth aspect of the invention is directed to an optical apparatus for measuring a relative amount of a plurality of fluorescent glomerular filtration rate molecules within a vascular system. The optical apparatus comprises a source of a first fluorescent excitation wavelength, a source of a second fluorescent excitation wavelength, a delivery optical path along which the first and second fluorescent excitation wavelengths pass, an excitation site to which the first and second fluorescent excitation wavelengths are delivered, a return optical path along which a first emitted fluorescence signal and a second emitted fluorescence signal pass from the excitation site, a first means for detecting an intensity of the first emitted fluorescence signal; and a second means for detecting an intensity of the second emitted fluorescence signal.

The optical apparatus of the fifth aspect of the invention may further comprise a first lens for focusing at least one of the first or second fluorescent excitation wavelengths onto the excitation site. A second lens may focus at least one of the first or second emitted fluorescence signals onto one of the first or second means for detecting. A third lens may focus the other of the first or second emitted fluorescence signals onto the other of the first or second means for detecting. A first condenser lens may be provided for minimizing an aberration associated with the first fluorescent excitation wavelength. A second condenser lens may be provided for minimizing an aberration associated with the second fluorescent excitation wavelength. A first dichroic filter may be positioned within the delivery optical path. A second dichroic filter may be positioned within the return optical path. A third dichroic filter may be positioned within the optical device between the delivery optical path and the return optical path.

A sixth aspect of the present invention is directed to a catheter for use in analyzing an operating condition of a kidney. The catheter comprises a tubular main member having a proximal end opposite a distal end and defining a passageway and a fiber optic cable extensible from the distal end. The catheter may further comprise an introducer connected to the tubular member at one end and having an opposite end insertable into a vascular system, and/or an insertion tool. A length of the fiber optic cable may be fluid sealed within the insertion tool. The insertion tool may include a first tubular member slidable within a second tubular member. The fiber optic cable may be held captive by a portion of the first tubular member. The insertion tool may be joined to a port of the tubular main member wherein the fiber optic cable passes through the insertion tool and into the tubular main member. The tubular main member may be joined to the introducer by a connector. The fiber optic cable may be extensible from the introducer upon relative movement between the first and second tubular members.

The first and second tubular members may be fluidly sealed.

The fiber optic cable may include a bend on a distal end insertable into a vascular system.

A seventh aspect of the present invention is directed to a catheter for use in analyzing an operating condition of a kidney. The catheter comprises a fiber optic cable, a fiber optic insertion tool about a length of the fiber optic cable having a first tubular member sealed to a second tubular member and capable of relative movement therewith, the fiber optic cable held attached to a portion of the first tubular member such that movement by the first tubular member transfers movement to the fiber optic cable, and a tubular main body sealed to the insertion tool, the fiber optic cable passing through a passageway in the tubular main body and extensible therefrom upon relative movement between the first and second tubular members.

The catheter may further comprise an introducer connected to the tubular main body. The introducer is insertable within a vascular system, and the fiber optic cable extensible therefrom.

The fiber optic cable may have a bend at one end. The one end is insertable within a vascular system.

An eighth aspect of the present invention is directed to a method of measuring a glomerular filtration rate in a mammalian kidney. The method comprises the steps of: providing a plurality of first fluorescent molecules; providing a plurality of second fluorescent molecules; introducing the first fluorescent molecules and the second fluorescent molecules into a blood stream of a mammalian subject; exciting the first fluorescent molecules with a first fluorescence excitation wavelength to generate a first fluorescence emission signal having a first fluorescence emission wavelength and exciting the second fluorescent molecules with a second fluorescence excitation wavelength to generate a second fluorescence emission signal having a second fluorescence emission wavelength; measuring an intensity of the first fluorescence emission signal and an intensity of the second fluorescence emission signal subsequent to the introducing step; and calculating a ratio of the first fluorescence emission signal to the intensity of the second fluorescence emission signal. The measuring and calculating steps may be performed at predetermined intervals and reported in at least substantially real time.

A ninth aspect of the present invention is directed to a method of measuring a glomerular filtration rate in a mammalian kidney. This method comprises the steps of: providing a fluid comprising a plurality of reporter molecules and a plurality of marker molecules in a predetermined ratio; introducing the fluid into a vascular system of a subject; and measuring a characteristic of each of the reporter and marker molecules after an elapsed time duration within the vascular system of the subject. This method may further comprise the steps of: calculating a ratio of the reporter molecule characteristic and the marker molecule characteristic subsequent to the measuring step; and reporting the ratio. The reporting step may be performed at a plurality of elapsed time durations. The calculating and reporting steps may be performed in at least substantially real time.

The reporter molecules may be capable of passing through a glomerular filtration barrier. The marker molecules may be less capable than the reporter molecules of passing through a glomerular barrier. The reporter molecules and the marker molecules may be fluorescent molecules. The reporter molecules and the marker molecules may comprise dextrans. The marker molecules may have a greater molecular weight than the reporter molecule. The reporter molecule may have a molecular weight between 1 kD and 150 kD. The marker molecule may have a molecular weight greater than 100 kD.

A tenth aspect of the present invention is directed to a method of measuring a glomerular filtration rate in a mammalian kidney. This method comprises the steps of: providing a source of light having a known wavelength; exposing a fluorescent molecule to the light source wherein the fluorescent molecule is excited within a vascular system of a mammalian subject for a predetermined time duration; and measuring a characteristic of the excited fluorescent molecule, the characteristic having a correlation to a condition of the vascular system.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 15 is a block diagram of a two compartment model;

FIG. 16 is an illustration of a dissembled catheter having an optical fiber.

DETAILED DESCRIPTION

Figure 1:
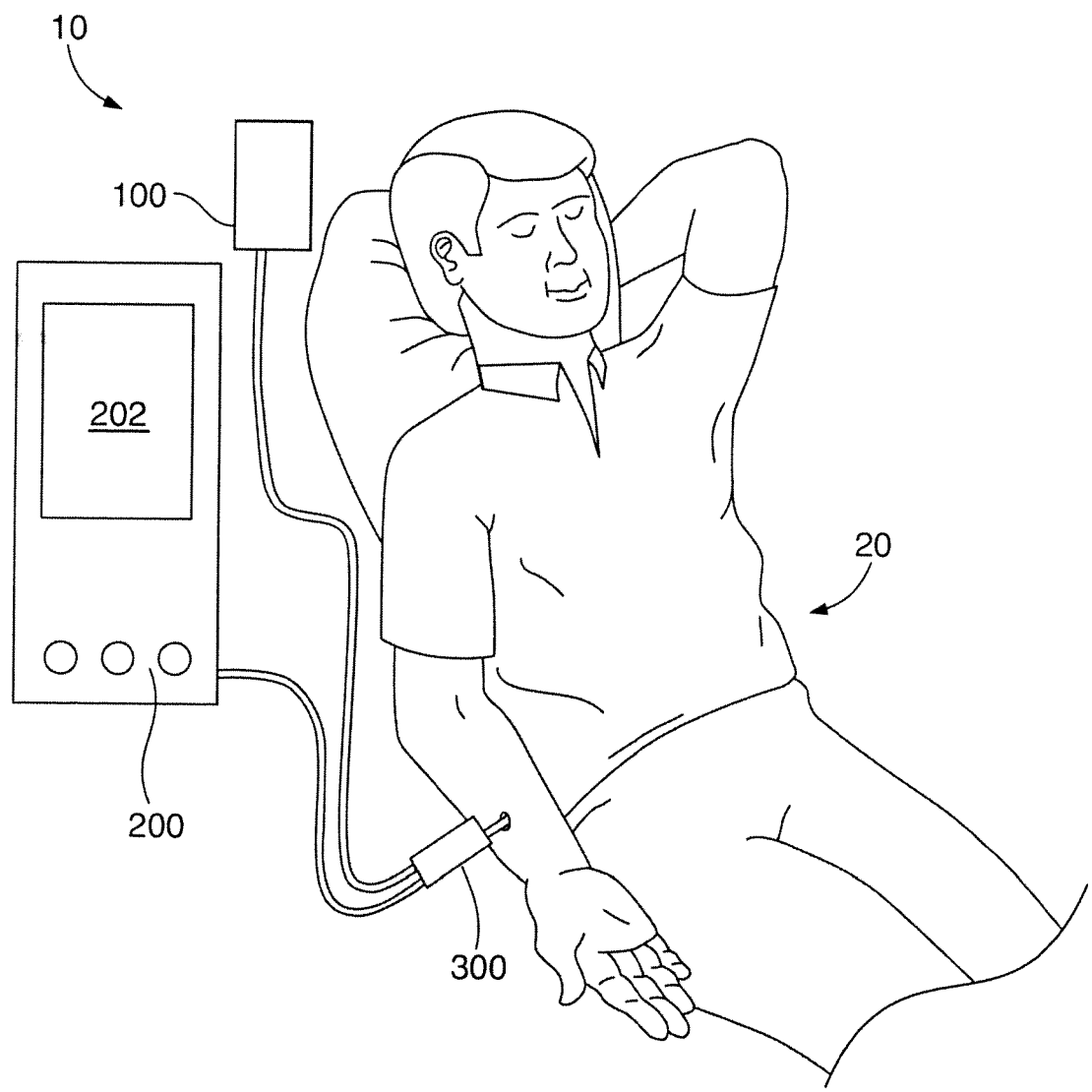
FIG. 1 is an illustration of an apparatus of the present invention utilizing a method of the present invention.

While this invention is susceptible of embodiments in many different forms, there are shown in the drawings and will herein be described in detail preferred embodiments of the invention with the understanding that the present disclosures are to be considered as exemplifications of the principles of the invention and are not intended to limit the broad aspect of the invention to the embodiments illustrated.

The inventors have found that a combination of both structural and functional markers of AKI presents a high level of clinical utility in diagnosing kidney function and kidney-related diseases. Thus, one objective of the present invention is to provide tests for analyzing and quantifying organ function and physiological parameters that have been difficult or impossible to measure in the past. The present invention focuses on a method and device for rapid detection of acute kidney injury and chronic kidney-related diseases. This development utilizes technology developed by and licensed from the Indiana Center for Biological Microscopy. Such technology is described in U.S. Provisional Patent Application No. 60/672,708, PCT Application No. US2006/014576, published as WO/2006/113724, and U.S. application Ser. No. 11/911,895, which are hereby incorporated by reference as if fully set forth herein. Specifically, figures of the apparatuses shown in FIGS. 6-9 of WO/2006/113724 and the descriptions of same at the paragraphs numbered 96 to 104 are directed to the technology utilized.

In early animal studies, this technology has proven efficacious in providing accurate and rapid measurement of the true Glomerular Filtration Rate (GFR)—the rate by which the kidney is able to filter waste products from the blood stream. While the need for disease diagnostics varies according to the specific disease, in kidney disease, GFR is the primary clinical indicator of injury, disease progression, or recovery.

GFR measures the amount of plasma filtered through glomeruli within a given period of time. It is clinically the most widely used indicator of kidney function. Physicians routinely use it for both diagnostic and therapeutic decisions. In fact, the National Kidney Foundation has now divided chronic kidney disease patients into five groups (I-V) based upon their estimated GFR (eGFR). This has assisted clinicians in recognizing and understanding the severity of the kidney disease in patients. It has also allowed for the initiation of appropriate therapies based on the patient's baseline GFR.

A variety of techniques such as radioactive and non-radioactive contrast agents, as well as radiographic renal imaging, can measure GFR rapidly. Plasma clearance techniques are based on measuring the plasma clearance of GFR marker molecules. By using radioactive markers, such as $^{51}$Cr-EDTA or [99]m Tc-DTPA ([99]m Technetium diethylene triamine pentaacetic acid), it has been reported that plasma clearance and GFR could both be determined independently using a radiation detector. Using radioactive GFR markers, such as $^{51}$Cr-EDTA and [99]mTc-DTPA ([99]m-Technetium diethylene triamine pentaacetate), in conjunction with a radiation detector, one can monitor GFR in patients with acute kidney injury at rates close to real-time. The measured plasma clearance shows excellent correlations with GFRs simultaneously measured using the standard method with urine collection. However, the use of radioactive GFR markers and the clinical difficulties in administering this test make this method unattractive. By using a fluorescent GFR marker, such as FITC-inulin, with a bolus intravenous infusion followed with drawing blood samples at multiple time points, one can accurately determine GFR. Potentially, with the development of a suitable contrast agent, magnetic resonance imaging (MRI) techniques can be very useful for providing kidney functional diagnostics. The downside of using such technologies is the low accessibility, associated high cost, difficulty repeating the study and the need to move the patient for the study.

Similarly, the plasma concentration of non-radioactive markers, e.g. iothalamate, determined by standard methods, such as high-performance liquid chromatography (HPLC), has also been used to evaluate renal function in critically ill patients. Such plasma clearance based GFR measurement techniques have been reported to have good time resolution in detecting changes of renal function in patients with severely impaired renal function. By using bolus infusion of a single fluorescent GFR marker, FITC-inulin, GFR has been determined by sequentially measuring the fluorescence signals in the blood samples drawn as a function of time after infusion. The inventors have expanded upon and enhanced this approach offering improved accuracy, rate of determination, and reduced exposure to potentially toxic radioactive molecules.

Inulin, a small fructose polymer that is filtered, and cleared from the body only by glomerular filtration, is a reference standard GFR marker. Other non-radioactive markers (such as iothalamate, iohexol, polyfructosan) and radioactive ones (such as $^{125}$I-iothalamate and $^{51}$Cr-EDTA) are also commonly used.

In clinical practice, endogenous markers such as serum creatinine and cystatin C are routinely used to estimate GFR, since the production and tubular reabsorption rates of these molecules vary significantly from different individuals. Cystatin C has received recent attention as a superior endogenous serum marker of GFR, compared to serum creatinine, as it is elevated up to a day earlier than creatinine in an ICU population with AKI.

The inventors have developed a minimally invasive device for direct measurement of GFR in mammalian subjects, such as humans, using a multi-photon microscopy method, preferably a two photon microscopy method. The method relies on reading two fluorescent molecules attached to different size dextran molecules. Dextran is a complex, branched polysaccharide made of many glucose molecules joined into chains of varying lengths (from 3 to 2,000 kD). Thus, another objective of the present invention is to provide both a method and apparatus using a catheter based fiber optic probe to read the fluorescent markers. This catheter can be placed into a vascular system, e.g., an arm vein of a mammalian patient, to allow the concentration of fluorescent markers to be monitored in real time, providing a direct measurement of GFR.

A rapid and accurate measurement of GFR in an early stage of acute kidney injury is important for diagnosis, stratification of extent of injury and therapeutic purposes. An advantage of the present invention is that it will rapidly identify and determine the extent of injury allowing for early treatment, including dialysis initiation, as well as enrollment and stratification for clinical studies. It could also be used to determine the effect of a clinical maneuver on GFR, such as volume resuscitation. Therefore, this technical advance is of major clinical importance, especially in high risk patients where intense surveillance is necessary for early diagnosis, injury stratification and determination of therapeutic potential.

The inadequacies of methods currently clinically used for estimating GFR are established both in literature and in practice. While progress is being made to identify biomarkers for detecting presence of injury, little progress has been made in finding a functional marker that is practical enough for broad acceptance. The inventors' method represents a true advancement in the ability to accurately quantify and track the degree of kidney function with near real-time efficiency. The inventors have also developed a device that is easy to operate in a busy medical environment—a critical adoption barrier in medical technology.

The optical technique developed by the inventors is based on plasma clearance measurements of a fluorescent bioreporter molecule and allows for the rapid, frequent, and safe evaluation of GFR. To further validate the values, other standard GFR tests, including but not limited to inulin clearance, may be performed. Upon comparison of these values, a correction factor may be applied to the data obtained using this novel method if needed.

Referring to FIG. 1, an apparatus 10 which incorporates a method of the present invention is illustrated. The apparatus 10 comprises a source of a GFR measurement composition 100, a kidney fluorescent detector 200, and a catheter 300. The GFR measurement composition 100, which comprises a plurality of reporter molecules and a plurality of marker molecules, is introduced into the blood stream of a human subject 20 via the catheter 300. The fluorescent detector 200 monitors the level of the GFR measurement composition within the blood stream and reports an operating condition of the human subject's kidney in at least substantially real time. This apparatus measures volume of plasma distribution based on a fluorescence of a marker molecule relative to the fluorescence of a reporter molecule. "Substantially real time" is intended to encompass the duration elapsed between measurement of the levels of the reporter and the marker within the blood stream, calculation of the operating condition of the kidney, and reporting of that condition. It is contemplated by the inventors that this elapsed time will be very near real time as to be negligible in relation to the prior techniques discussed above.

The GFR Measurement Composition

By utilizing intravital multi-photon microscopic imaging of the kidney, the inventors have quantified glomerular filtration and tubular reabsorption processes independent of each other. The inventors have developed ratiometric imaging techniques permitting quantitative analysis of fluorescence signals within local regions of the kidney using multi-fluorescent probe experiments. To measure GFR by plasma clearance, the inventors use a fluorescent GFR reporter molecule, e.g. FITC dextran, together with a large different fluorescent marker molecule that does not pass through the glomerular filtration barrier. This large fluorescent marker serves to quantify the plasma volume of distribution in the vascular space and allow for the ratiometric technique.

The inventors have been able to quantify plasma clearance of the fluorescent GFR marker by examining the ratio of fluorescence intensities of the two molecules from within the blood vessel regions of the image. GFR can be rapidly determined using this ratio technique. This method has been tested in a number of animal models. Since the fluorescent signals are being measured from within the blood vessels to quantify the kinetics of plasma clearance, the ratio signal of the two fluorescent molecules is independent of the body location where the measurement is performed.

To measure GFR accurately, the inventors have determined that the ideal GFR marker molecule should be stable within the vascular compartment during the study and have a glomerular sieving coefficient (GSC) of 0.0, be retained within the vasculature, and it should not be, or should substantially not be, secreted, reabsorbed, or filtered within the kidney and may have a molecular weight greater than 100 kD. "Substantially" as used here is limited to ±5%. Satisfying these conditions, the GFR would be equal to the urinary clearance of the reporter after its intravenous infusion. In theory, one could use a GFR reporter with any known GSC that is greater than 0. The preferable marker molecule is a sulphorhodamine 101 having a molecular weight greater than 100 kD.

Figure 2:
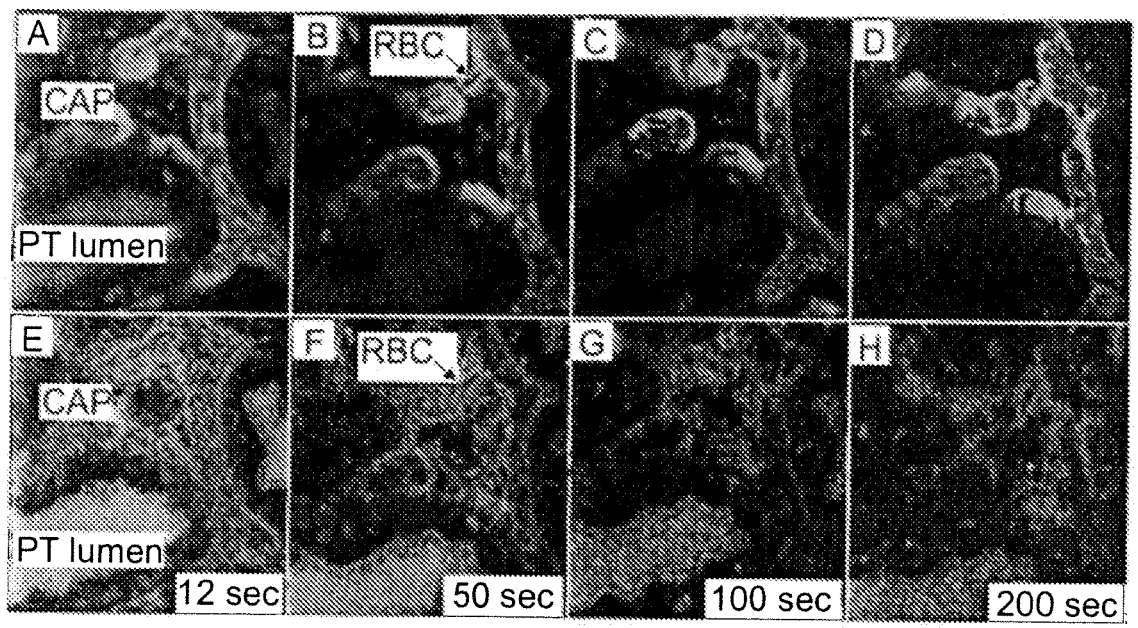
FIG. 2 is a series of micrographs showing renal clearance of a small molecular weight dextran in a normal rat as visualized by intravital 2-photon microscopy. Micrographs taken from a time series reveal localization of both a small FITC-inulin (5.5 kD) (lower series of micrographs) and a large 500 kD Texas Red® dextran (upper series of micrographs) within the capillaries (CAP). The inulin is rapidly filtered into the proximal tubular lumen (PT lumen) resulting in a steady decrease in fluorescence signal over time (panels E, F, G, & H). In contrast, the 500 kD dextran is not cleared and its signal remains constant within the capillaries (panels A, B, C, & D). The fluorescence seen in the PT lumen in Panel A, B, & C is not clearance of the 500 kD dextran but bleed through emissions from the FITC-inulin. The current approach of sequential excitation and acquisition with separate LED's will minimize this bleed through phenomenon.

FIG. 2 contains several fluorescence intensity images of the kidney from a live and healthy male rat. These images were taken as function of time after a bolus intravenous infusion of a dye mixture containing a FITC-inulin (5.5 kD) and 500 kD dextran labeled with a sulforhodamine 101, i.e. Texas Red®. The fluorescence intensity signal from FITC-inulin is shown in the lower series of micrographs, and the 500 kD Texas Red® dextran intensity is shown in the upper series of micrographs. At about 12 seconds after dye infusion, the fluorescence intensity was seen in both the capillaries of the kidney and in the proximal tubule (PT) lumen. The variations in the blood vessel over time indicate that both the FITC-inulin and 500 kD Texas Red® dextran were in these blood vessels. At 50 seconds, the FITC-inulin was already decreasing in intensity in the capillary and in the PT lumen as a result of immediate plasma clearance (glomerular filtration) of this molecule. This was not true for the red 500 kD dextran where the capillary intensity was similar to the 12 second value. A red blood cell (RBC) appears as a dark object as it excludes dye. At 100 and 200 seconds the FITC-inulin intensity continued to decrease in the capillary and in the PT lumen as filtration continued to remove it from the body. This again was not true for the 500 kD Texas Red® dextran which did not change in intensity during this time interval as it was not filtered. Consequently, the relative strength of the intensity from the blood vessels increases indicating a relative increase in the 500 kD Texas Red® dextran to FITC-inulin concentration ratio due to plasma clearance of the FITC-inulin. This type of time-series image collection contains dynamic information about a given molecule passing through the glomerular filtration barrier of the kidney, and becoming part of the filtrate. This provides the basis for the inventors' measurement of plasma clearance rates and GFR.

Figure 3:
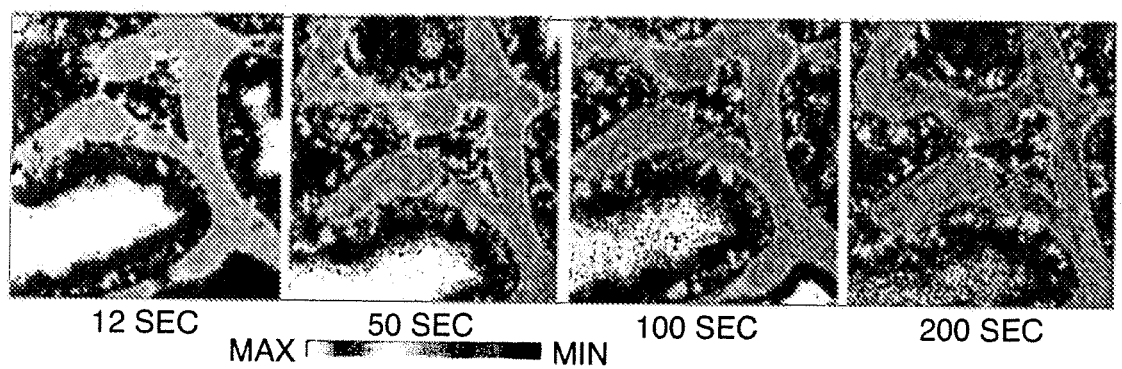
FIG. 3 is a series of micrographs showing the intensity ratio of FITC-inulin to the 500 kD Texas Red® dextran with the 500 kD Texas Red® dextran staying in the blood stream a longer time after dye infusion due to the larger molecular size.

To quantify molecular filtration dynamics, the inventors used the intensity ratio of the FITC-inulin and the 500 kD Texas Red® dextran (See FIG. 3). The intensity ratio from the blood vessels in FIG. 3 changes over time with a change of relative concentrations of the two dyes. Since the 500 kD dextran molecules are minimally cleared from the vascular culture, not by the kidneys, due to its large size, it remains stable in the plasma for a long time after infusion. Typically, there was no noticeable intensity drop from the 500 kD dextran within the time period following a dye infusion (anywhere between 5-30 minutes). This resulted in a decreasing intensity ratio visualized over time. It is this type of ratio that greatly minimizes the problems with using fluorescence intensity as a read out for biological studies.

Figure 4:
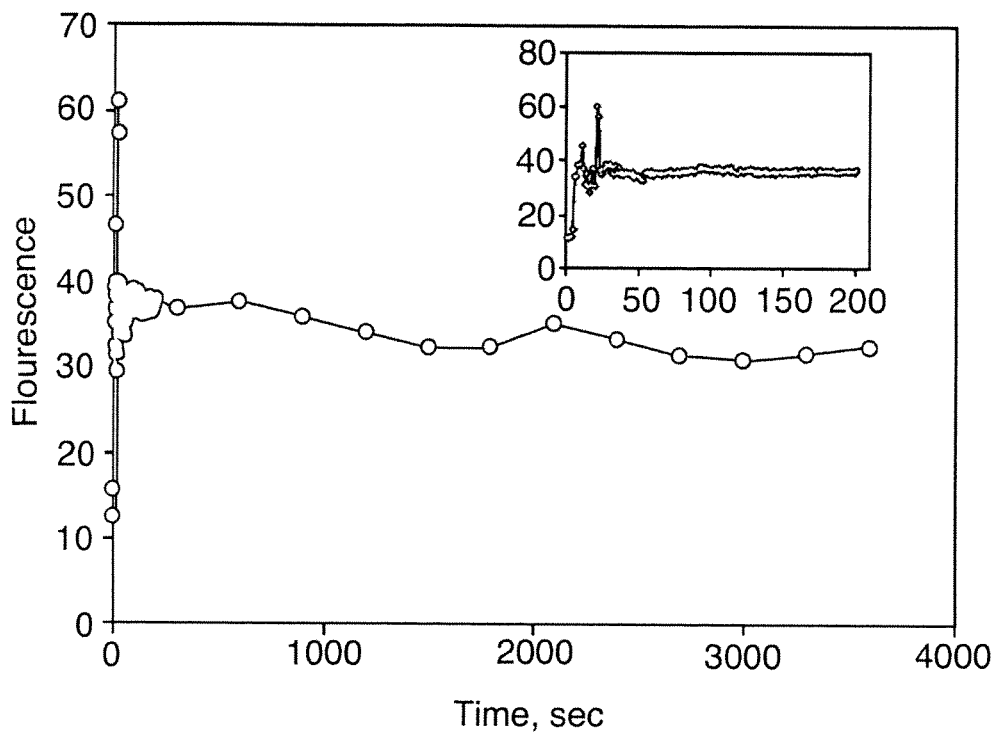
FIG. 4 is a plot of the intensity time-series of the 500 kD FITC dextran measured from a blood vessel following a bolus infusion up to 60 minutes.

The inventors have also used a 500 kD fluorescent dextran for similar studies in order to further minimize filtration and extend the dye's plasma survival time. FIG. 4 is an example of the intensity time-series of the 500 kD FITC dextran measured from a blood vessel following a bolus infusion up to 60 minutes. The initial intensity spike (see inlet) was due to dye injection and fast distribution of the dye molecules into the whole plasma volume. It did not show significant intensity drop for the rest of the curve. Effectively, the decrease of the fluorescence intensity ratio of labeled inulin to labeled 500 kD dextran correlates with the concentration decrease of the labeled inulin.

Figure 5:
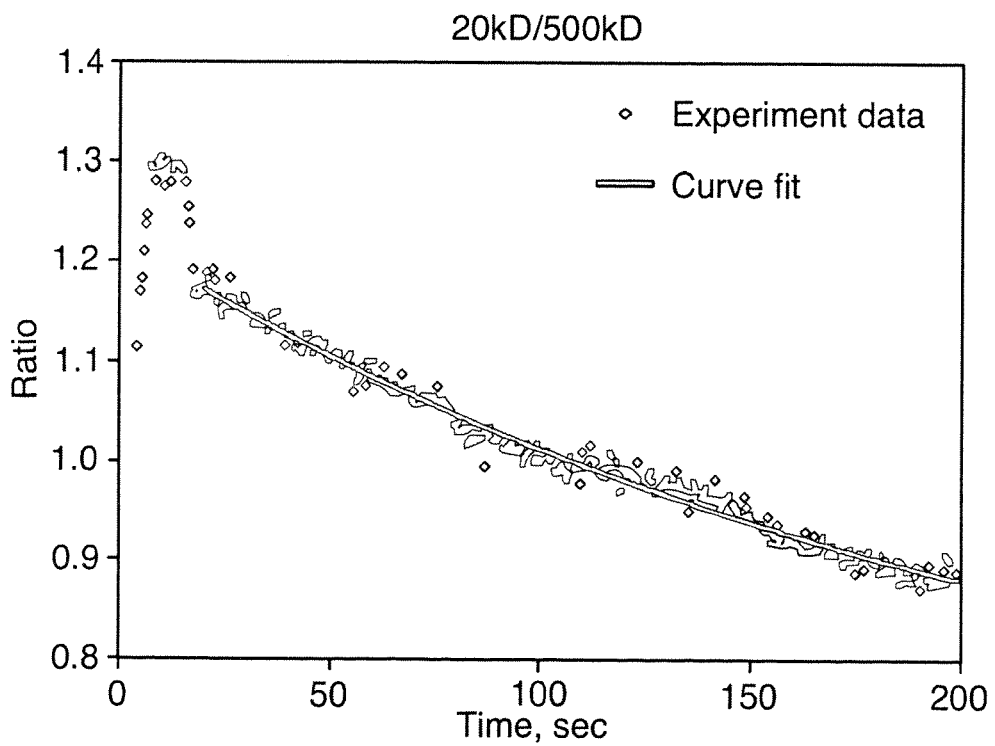
FIG. 5 is a plot of the intensity ratio of a bolus injection of 20 kD FITC dextran to 500 kD Texas Red® dextran as a function of time along with the result of a least square fit.

FIG. 5 is a plot of the intensity ratio of a bolus injection of 20 kD FITC dextran to 500 kD Texas Red® dextran as a function of time along with the result of a least square fit. Each data point in FIG. 5 was the average ratio value of the same region from a blood vessel extracted from an image time-series (such as the images shown in FIG. 3). The data points were plotted every 0.5 seconds up to 200 seconds. The decay occurred in two phases, the initial phase and the clearance phase (or the filtration phase/elimination phase). The gradual increase of the initial phase was due to relative dye distributions and accumulations in the kidney following IV injection. The highest point (around 12 seconds) of the curve marks the starting point of the clearance phase and correlates with the beginning of the appearance of FITC-inulin in the proximal tubule.

The data points of the clearance phase fit well with a single exponential. The inventors obtained a 20 kD FITC dextran plasma clearance rate constant, k, of 0.00458 ($s^{-1}$) (using 95% confidence limits).

Following a bolus infusion of GFR reporter molecules, the plasma concentration of the GFR reporter molecules decreases as a function of time due to renal clearance. By acquiring plasma samples at different time points, one can either directly calculate or perform least square fit of the time trace to retrieve the plasma clearance rate constant (k). GFR can then be determined according to the equation:

$$GFR = kV_d \quad (1)$$

where k is the plasma clearance rate and $V_D$ is the volume of distribution into which the GFR marker is diluted. GFR measured using this technique has been validated in patients with stable renal function as well as in rodents and proven to be accurate and correlated well with what was measured using other methods.

Figure 6:
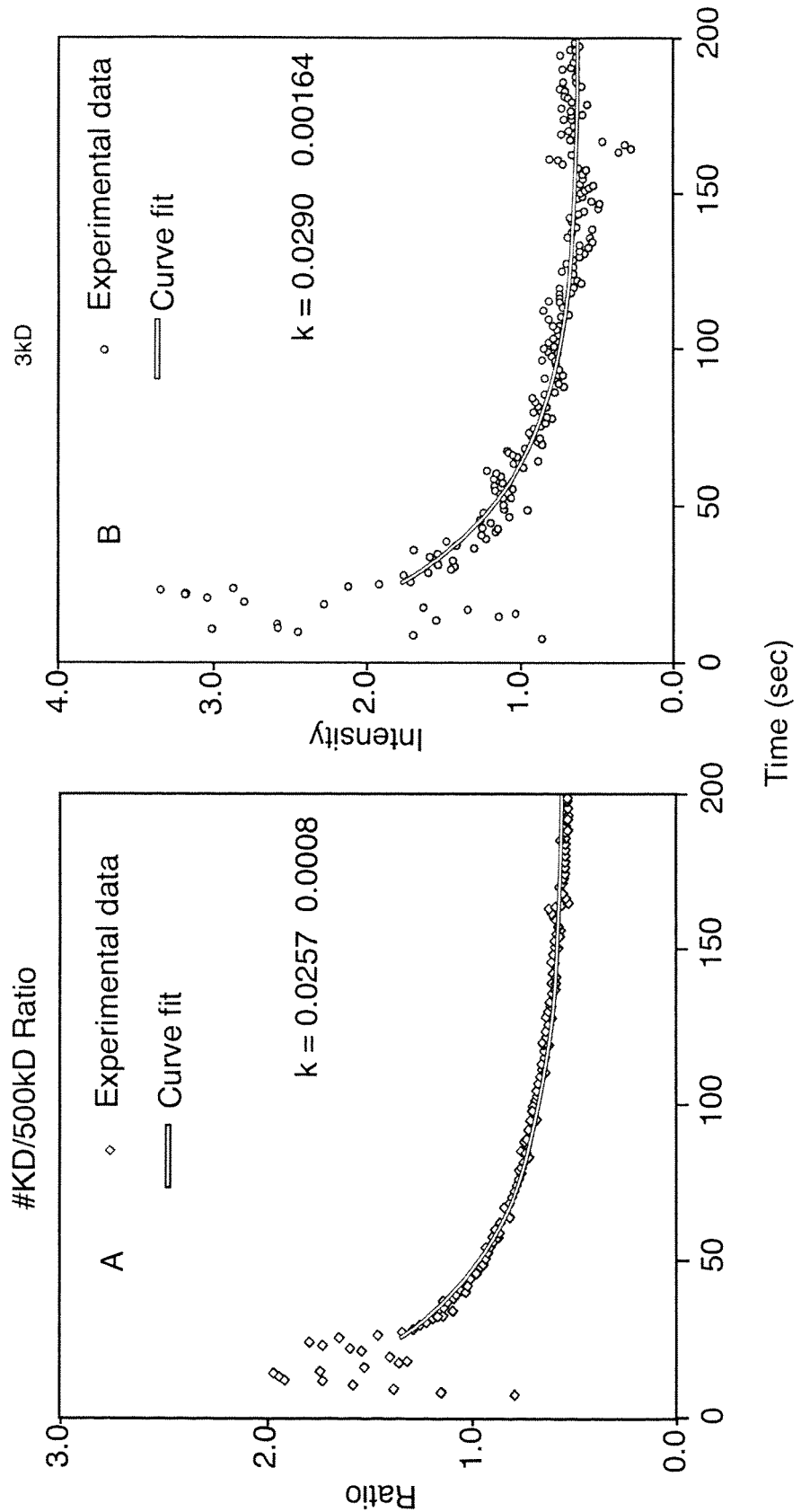
FIG. 6 is a comparison of plots between using a ratio technique and directly using intensity for measuring plasma clearance.

A comparison between using the intensity ratio and directly using the intensity value of a 3 kD FITC conjugated dextran (3 kD FITC dextran) for measuring the clearance rate is shown in FIG. 6. The chief differences are significantly less noise and better identification of distribution phase.

The intensity fluctuations of the 3 kD FITC dextran alone were quite significant (FIG. 6-B). Consequently, the fitting result of the clearance rate constant k contained larger errors and was less defined. In contrast, the intensity ratio (between 3 kD FITC dextran and a 500 kD Texas Red® dextran) had significantly less noise, and the measured clearance rate constant k was much better defined with only 3% error. This was partially because fluorescence intensity is typically very sensitive to even a slight change in microscope focus and movement of the sample. The intensity ratio, on the other hand, is insensitive to minor changes in imaging depth and motion. The inventors are focusing on the fluorescence signals from the blood. Furthermore, the intensity signal of a dye from the blood can change when the blood flow rate changes. However, the relative intensity ratio between two molecules does not change even when the blood flow rate or blood volume changes (assuming there is no clearance). This is because both dye molecules are present in the blood and move together. The method developed by the inventors limits this problem.

The separation between the initial dye distribution and the clearance phase is well-defined using the intensity ratio. When using the intensity of a single dye alone, it is more difficult to determine at what time point the clearance phase begins. The highest data point in the intensity curve typically does not correlate in time with the appearance of the smaller molecule in the proximal tubule lumen. Therefore, the dye distribution and the filtration phases are convoluted in the intensity only curve. Using multi-photon microscopy approaches allow such correlations and is highly beneficial.

It is believed that purity, in terms of size distribution or molecular weight, of the dextrans is vitally important. In addition, the distribution of molecular weight plays an important role in how well GFR can be measured. Even though dextrans are widely used in medical applications, these previous applications did not require the more stringent size control needed for use in the present invention.

Figure 7:
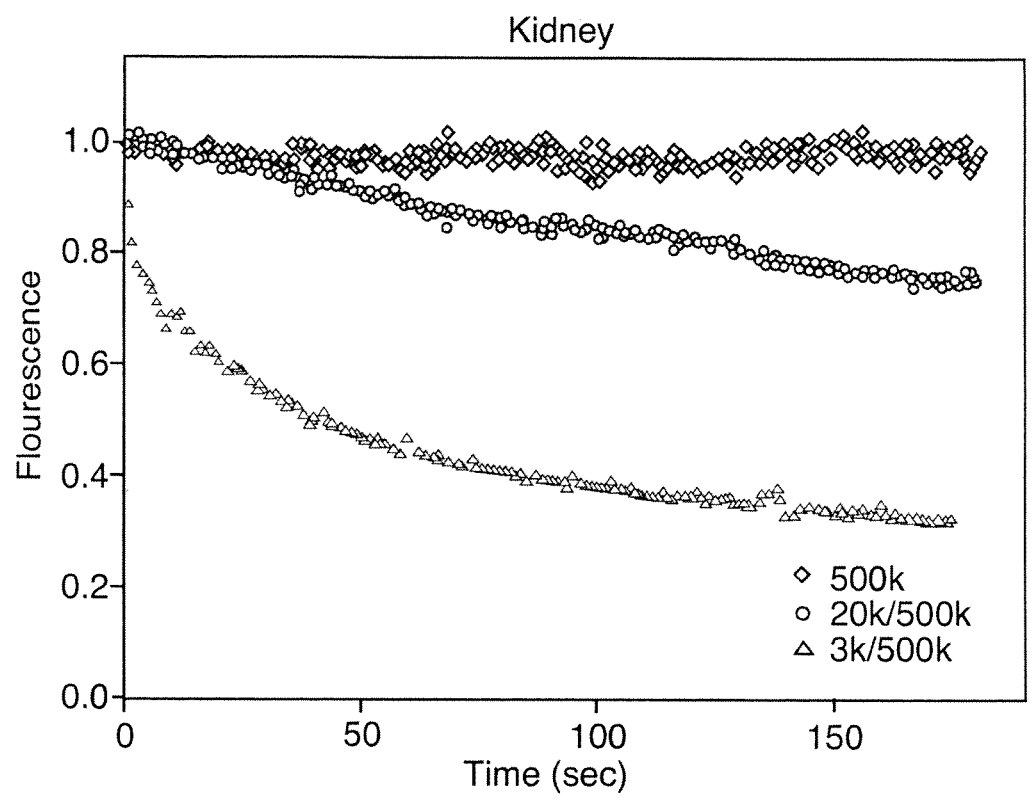
FIG. 7 is a plot showing the kidney vascular plasma intensity ratios resulting over time from two rats after bolus infusion, one with a mixture of 3 kD FITC dextran and 500 kD Texas-Red dextran and the other with 20 kD FITC dextran and 500 kD Texas Red® dextran.

Referring to FIG. 7, a plot of intensity values obtained from two rats after bolus infusion is illustrated. One rat was infused with a mixture of 3 kD FITC dextran and 500 kD Texas Red® dextran. The second rat was infused with 20 kD FITC dextran and 500 kD Texas Red® dextran. The plot shows a rapid decay with the 3 kD/500 kD fluorescence ratio curve. This indicates a fast clearance with movement into the interstitial space. However, a substantial part of it is due to non-renal plasma clearance as seen from 10 kD dextran data of liver imaging illustrated in FIG. 8.

Figure 8:
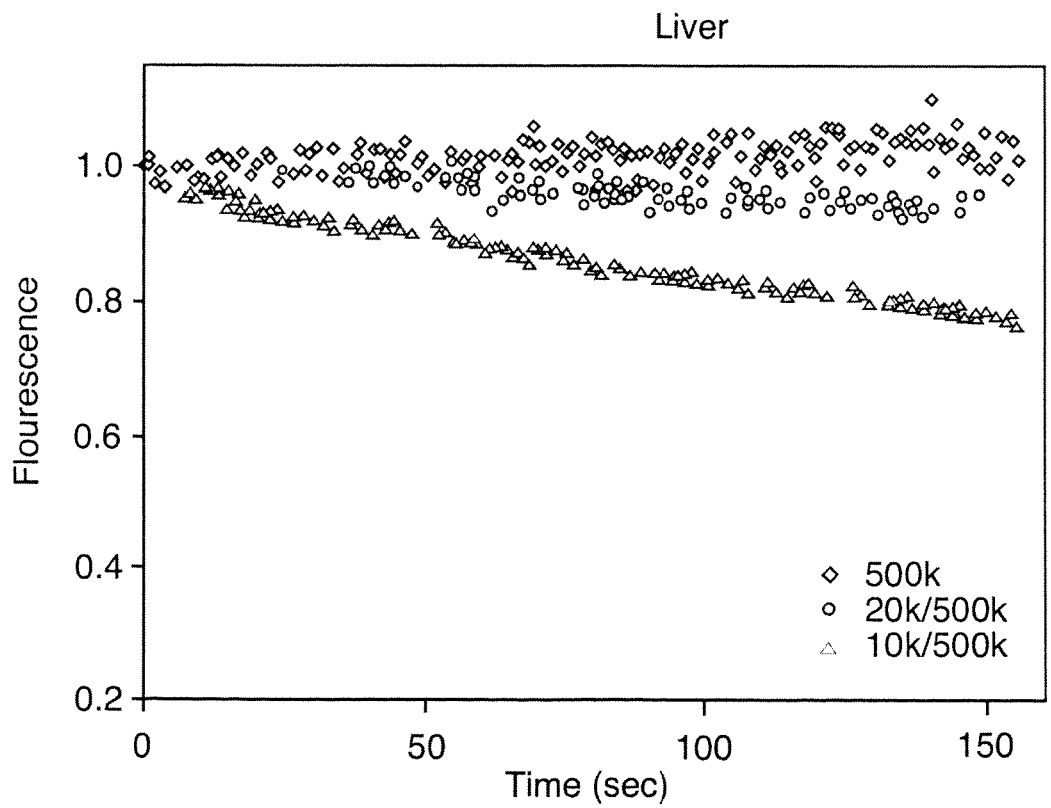
FIG. 8 is a plot showing liver vascular plasma intensity ratios over time from two anephric rats, one injected with a mixture of 10 kD FITC dextran and 500 kD Texas Red® dextran, the other with a mixture of 20 kD FITC dextran and 500 kD Texas Red® dextran.

FIG. 8 was generated from a pair of anephric rats (with both kidneys removed). One of the rats was injected with a mixture of 10 kD FITC dextran and 500 kD Texas Red® dextran. The other rat was injected with a mixture of 20 kD FITC dextran and 500 kD Texas Red® dextran. The 10 kD/500 kD ratio curve shows that there is clear evidence that non-renal plasma clearance of 10 kD dextran is still substantial. Meanwhile, the 20 kD dextran, which can be filtered by glomeruli, shows minimal non-renal plasma clearance. Therefore, it can be used to determine GFR.

Additionally, smaller molecules of 3 kD to 5 kD as reporter molecules in conjunction with a two compartment kinetic model can be used to measure organ function. Thus, the inventors have determined that the preferred molecular weight of the filtered molecule to be within the range of 3 kD to 500 kD, more preferably 3 kD to 150 kD, still more preferably 3 kD to 150 kD, still more preferably 3 kD to 70 kD, still more preferably 3 kD to 5 kD, and most preferably on the order of 5 kD, or any range or combination of ranges therein. The method also contemplates the use of known common sizes such as 10 kD and 500 kD dextrans as well less common sizes 20 kD, 70 kD and 150 kD. An amino fluorescein dextran is preferred.

Fluorescent Detector

The fluorescent detector 200 includes software for reading and reporting data, a user interface 202 to control the apparatus 10 and review results, and an apparatus for sending and receiving fluorescent signals 204 (see FIGS. 9, 10, and 12-14). This unit 200 is designed to be compatible with a standard IV pump stand, or it can be operated on a table top. It incorporates a battery backup system that is capable of running for 2 hours without connection to AC power.

The user interface 202 is capable of being used by any clinician. It includes touch screen technology for most of the software user interface. This provides flexibility in how the data is shown to the clinicians.

Based on the body of work done to perfect the ratio technique using multi-photon microscopy, the inventors determined that a fiber optic catheter placed in the blood stream of a subject would be capable of measuring the fluorescent molecules. The current method of using multi-photon microscopy is responsible for generating much of the variation due to the drop off in fluorescence intensity as the tissue is penetrated more deeply. Using a fiber optic catheter as disclosed herein will eliminate these variations since the measurements will be taken in real time, or substantially real time, directly in the blood. The fiber optic catheter is explained in more detail below.

Figure 9:
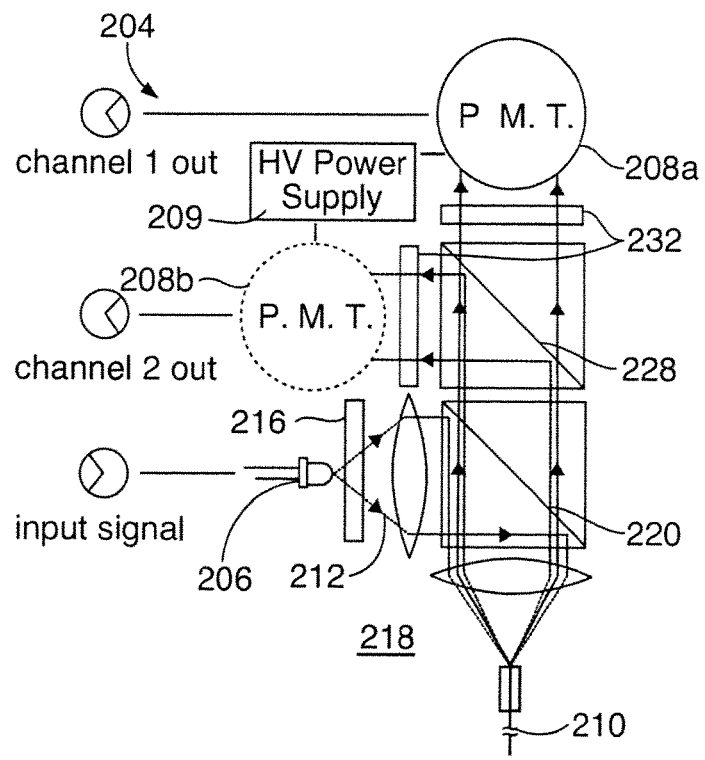
FIG. 9 is a block diagram a diagnostic apparatus of the present invention.
Figure 10:
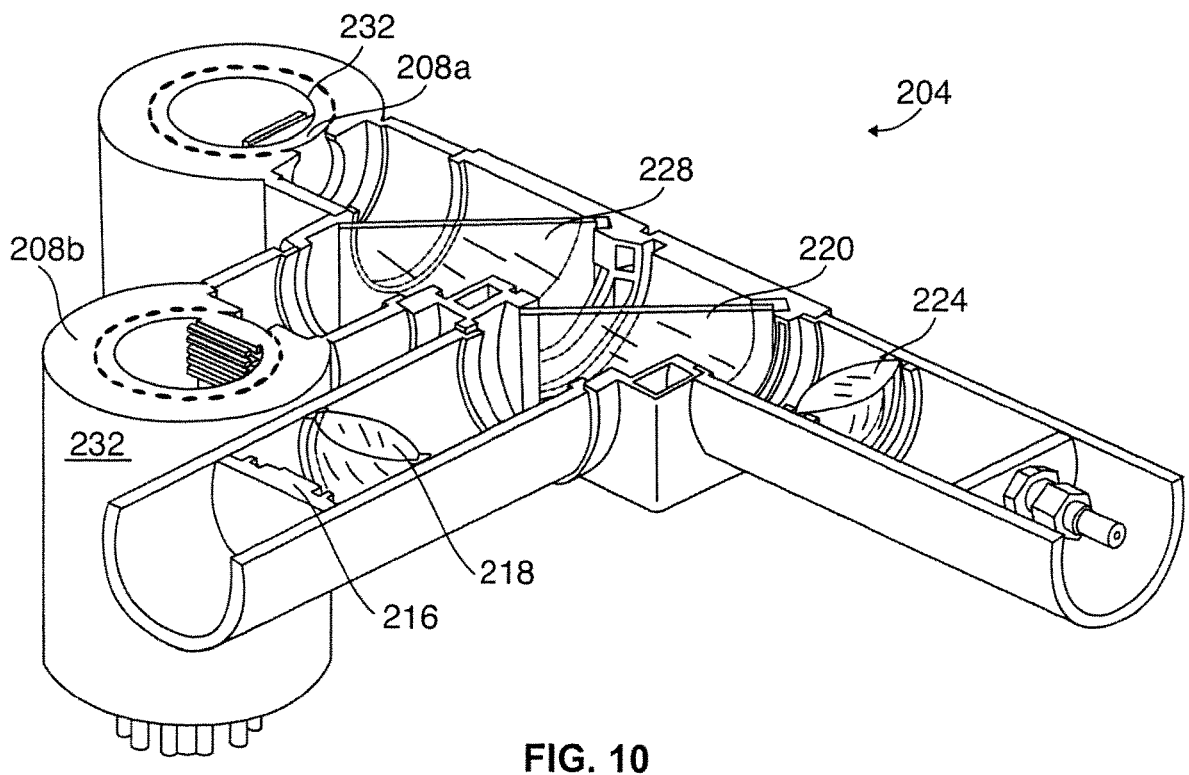
FIG. 10 is a model of the apparatus of FIG. 9.

FIGS. 9 and 10 illustrate a two channel apparatus 204 using a single multi-colored LED 206 (light emitting diode) as a light source. An objective of this apparatus 204 is to determine how much fluorescent signal would be returned from a fiber optic element 210. FIGS. 9 and 10 show both a diagram and computer model of the optical system used in this device. The apparatus includes photo multiplier tubes (PMT) 208a,b as detectors, since these devices have well-known characteristics. Alternatively, the detector may be a photo detector, a solid state detector, a charge-coupled device, or any other equivalent device without departing from the spirit of the invention. This apparatus may have one or more power supplies 207,209, and/or controllers, for providing power to the LED 206 and PMTs 208a,b.

An optical path 212 focuses the light from an LED source 206 through a selection of band pass 216 and dichroic filters 220, then onto the fiber optic element 210. An excitation light is then passed down the fiber optic element 210 into a test solution chosen to simulate the approximate level of fluorescent dextrans in a blood stream. The fiber optic element 210 is generally a fiber optic cable in the range of 0.5 to 1 mm in diameter or even smaller.

Once excited, a small portion of the fluorescence signal then passes back through the fiber optic element 210. The signal then passes through a focusing lens 224, dichroic beam splitter 228 and band pass filter 232 before landing on the cathode of the PMT 208a.

Figure 11:
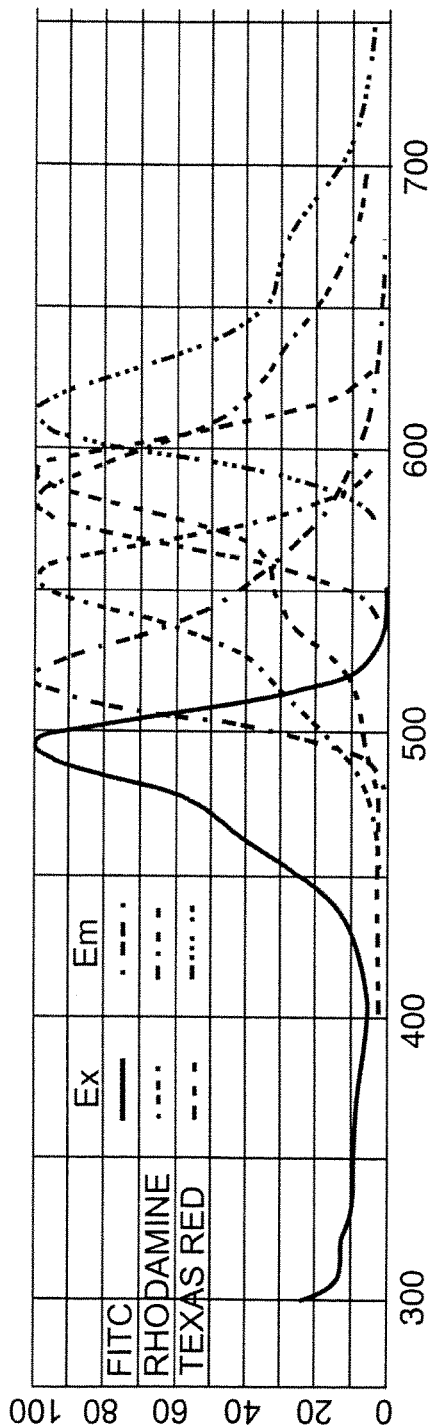
FIG. 11 is a plot of excitation and emission spectra of FITC, rhodamine and Texas Red® dyes.

An easily detectable fluorescent signal is measured from the PMT 208a,b for fluorescein dye. This dye has an excitation peak of about 494 nm and emits light in a broad band of wavelengths centered on 519 nm. Fluorescein dye is only one example of a marker dye. A rhodamine dye may also be used; however, the LED source 206 must have sufficient intensity to excite the rhodamine dye. The spectral response of fluorescein, rhodamine and Texas Red@, can be seen in FIG. 11.

The emergence of white LEDs based on adding a phosphor to the LED die may be used in the present device 200, but the narrow spectral bandwidth associated with standard LEDs is superior for reducing background light. The intensity of the light source and how efficiently energy can be delivered to the fiber optic 210 is critical.

Laser diodes may be used as a substitute for LEDs. The laser diode provides additional light energy which may allow a reduction in the concentration of dye markers in the blood stream. However, most of the wavelengths available are not ideal for the preferred fluorescent molecules of fluorescein and sulforhodamine 101.

LEDs from several vendors have been evaluated. Several LEDs meet the needs of the apparatus. These LEDs provide the best flux density per unit area and work well with the filters providing excellent elimination of off wavelength background.

For fluorescein, a LED490-03U made by ROITHNER LASERTECHNIK GmbH of Austria may be chosen. This LED has a peak wavelength of 490 nm for fluorescein excitation. This LED is rated at 1.2 mw. Alternatively, for fluorescein, an XREBLU-L1-0000-00K01 LED made by Cree Inc. of Durham, N.C. is preferable. This part is a high power surface mount LED with good thermal characteristics. The peak wavelength for this application is 485 nm with a minimum flux output of 30.6 lumens. A surface mount part that can be sorted to have similar characteristics may be substituted for this part.

For sulforhodamine 101 excitation, an 828-OVTL01LGAAS from OPTEK, having distribution in North America and throughout the world, with a peak wavelength of 595 nm, may be used. This surface mount LED has a higher flux density, so it can be run at lower power settings to minimize wavelength thermal drift. The target output power for the 1 mm fiber optic will be about 50 microwatts. For sulphorhodamine 101 excitation, an XRCAMB-L1-0000-00K01 LED from Cree Inc. of Durham, N.C. is preferable. LEDs of this type can be sorted for peak wavelength over the range of 585 nm to 595 nm. A peak output of 590 nm has been chosen for the application. These are high power surface mount LEDs with good thermal characteristics. The luminus flux output of this LED is also 30.6 lumens.

Filter selection is critical to performance of this system. Since the fluorescence signal returning through the fiber optic 210 will be many orders of magnitude below the excitation energy, filter blocking and bandpass characteristics are critical to proper performance. The fluorescent markers which have been used in microscopy and other applications for many years are well known in the art. Thus, excellent filter sets are available from a variety of manufacturers such as SEMROCK of the United States. These filters are ideal for this application.

Figure 12:
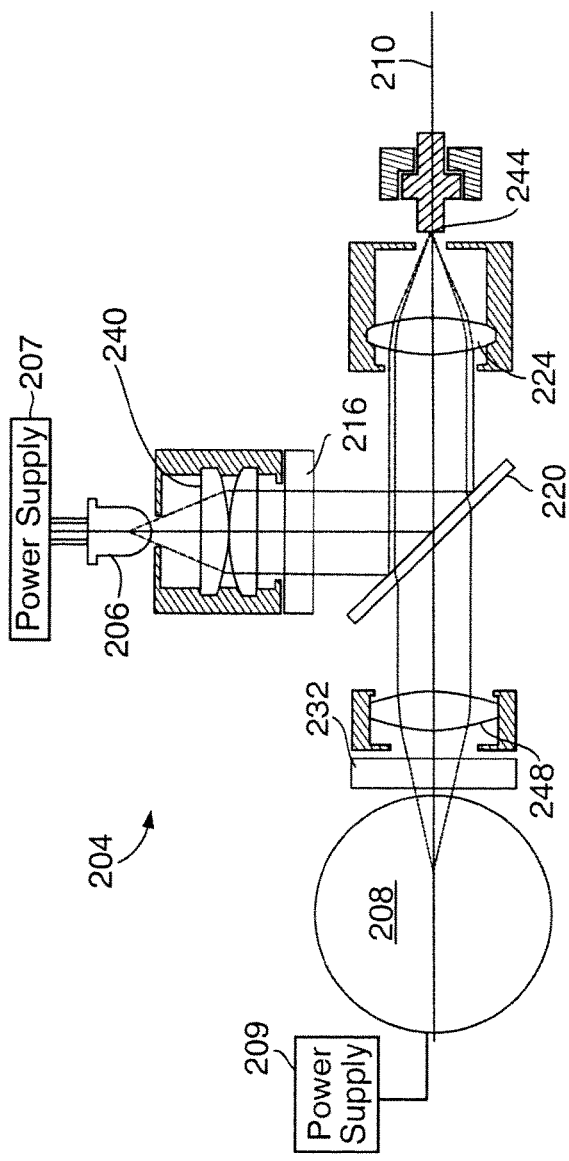
FIG. 12 is a block diagram of a single channel optical system.
Figure 13:
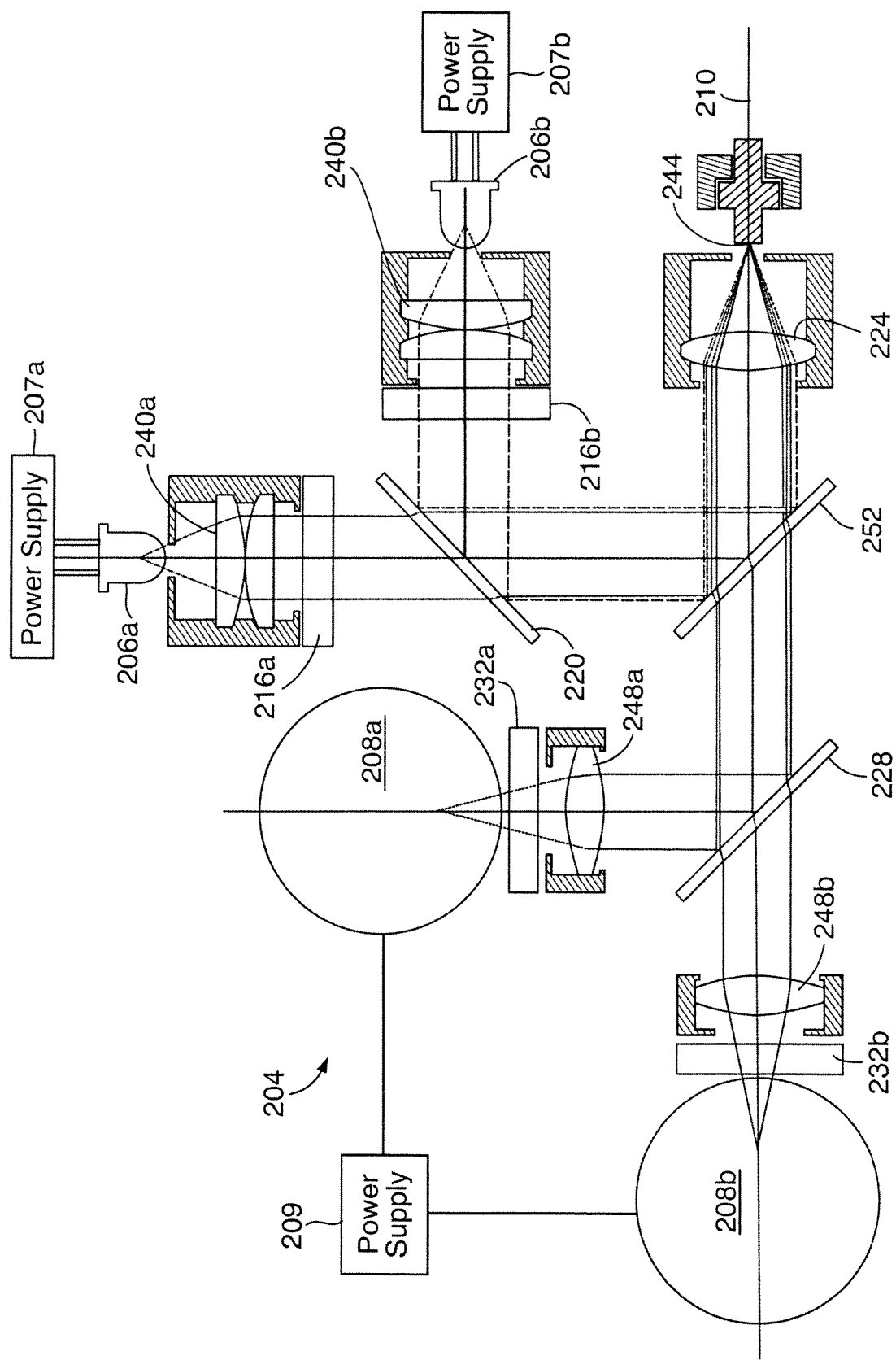
FIG. 13 is a block diagram of a two channel optical system.

Two additional apparatuses for sending and receiving fluorescent signals 204 have been contemplated by the inventors. These apparatuses are illustrated in FIGS. 12 and 13 and are aimed at improved optical geometry. A single channel apparatus is illustrated in FIG. 12. One objective of the single channel device is to improve the signal to background ratio and determine the target signal strengths for the fluorescently tagged dextrans in whole blood. An improved optical geometry has significantly reduced the background levels over an order of magnitude. This new optical geometry and fiber coupling has provided us with a 30 to 1 signal to background ratio.

FIG. 12 is a block diagram of a single channel optical system. The single channel device shown in FIG. 12 uses a simple optical design. Light from a 490 nm LED 206 is relayed through a band pass dichroic filter 220, then focused onto the fiber optic surface mount adaptor (SMA) connector 244. A simple condenser lens element 240 is used to minimize spherical aberrations that would limit ability to focus onto the small 0.5 to 1 mm fiber optic target 210. The fiber lens 224 works as both a final focusing element for the source light and the initial collimator for the fluorescent emission. The fluorescent emission light is relayed back through the dichroic filter 220 and refocused onto the PMT 208. Simple bi-convex lenses 248 are used for this since the target size on the PMT 208 is not critical, and a FITC emission filter is provided as a band pass filter. Close attention is given to stray light and reflections in this system by utilizing good light absorbing coating materials in the component construction.

Figure 14:
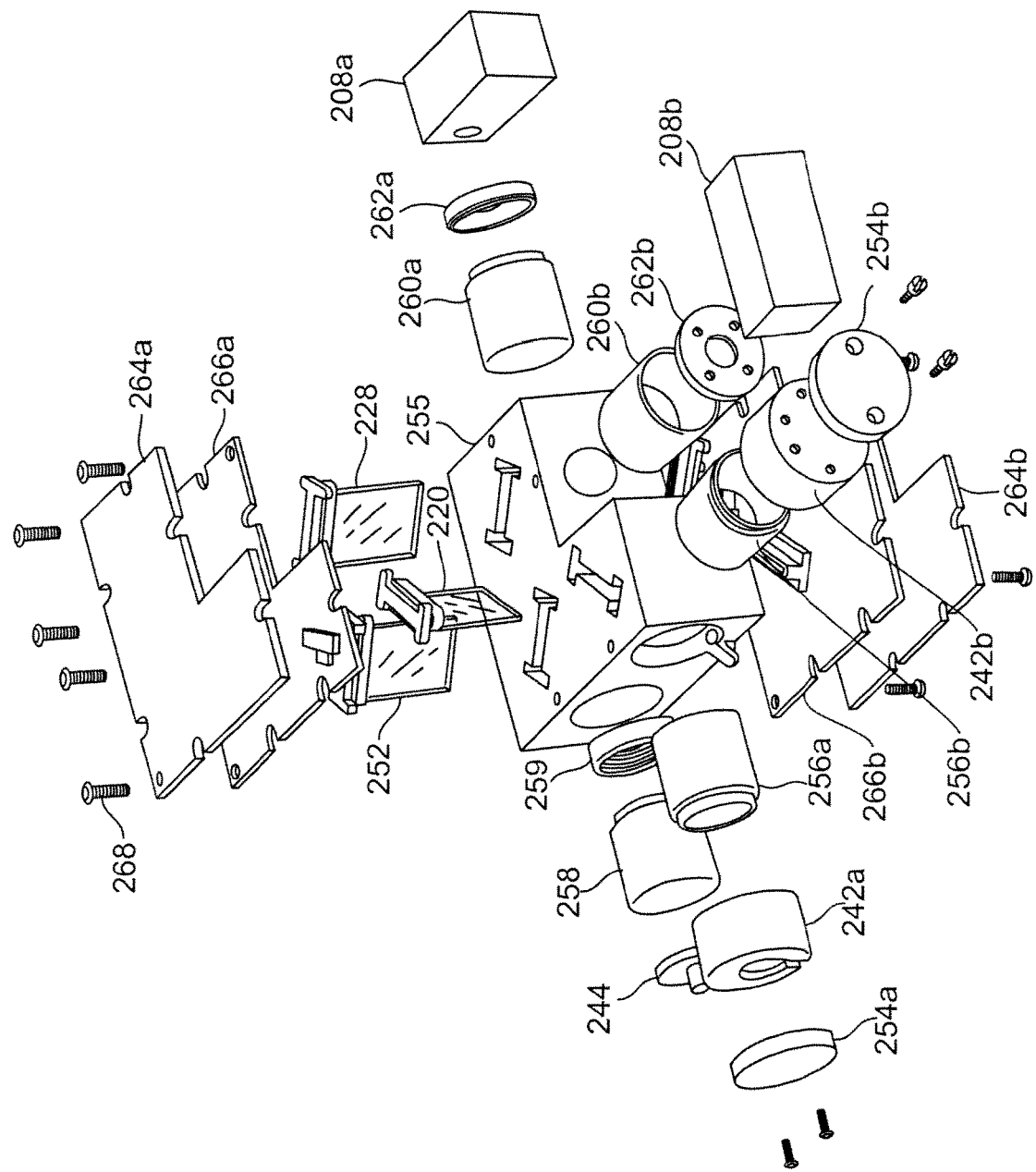
FIG. 14 is an exploded view of the two channel optical system of FIG. 13.

Referring to FIGS. 13 and 14, a two channel optical system is illustrated. Similar components to those chosen in the single channel design are used in the two channel design. The main differences are an additional dichroic filter within holders 254a,b and spaced from a main block 255 by spacers 256a,b used to combine light from the 490 nm LED 206a and 595 nm LED 206b together. Each source utilizes its own condenser lens assembly 240a,b and band-pass filter 216a,b, a 595 nm filter and a 490 nm filter respectively, within holders 242a,b. The light beams from the LEDs 206a,b are then relayed through a special dual band dichroic filter 252 before being focused by the lens 224 onto the fiber coupler 244, specifically the fiber optic target 210. This dual band filter is readily available from SEMROCK. The emission from both fluorescent molecules then travels back through the fiber optic cable 210. The fiber lens 224 is attached to main block 255 within holder 258 and ring 262 and is used to collimate this light for relay back through the dual band dichroic filter 252 and then split to the appropriate PMT 208a,b using a final emission dichroic filter 228. Each PMT assembly 208a,b has a final focusing lens 248a,b and an emission filter 232a,b, preferably a FITC emission filter and a sulphorhodamine 101 emission filter respectively, within holders 260a,b and PMT adaptors 262a,b. Main block 255 is closed by sealing plates 264a,b and gaskets 266a,b with fasteners 268

An electrical circuitry contains a microcontroller to control both the pulse rate to the LEDs 206a,b and synchronize the readings from the PMTs 208a,b. The LEDs 206a,b are energized for a short time at a frequency of 100 Hz. At no time are both LEDs 206a,b illuminated, eliminating some of the bleed through of the two fluorescent markers. A high speed 16 bit analogue/digital converter is used to read the PMTs 208a,b and average the data. A laptop computer may be used for the software component of this system, or the electrical circuitry, microcontroller, and software may be housed within the fluorescent detector 200.

Mathematical Model

A two compartment mathematical model may be used to calculate GFR from the intensity ratio of the two tagged dextran molecules. This model may be included in software which may be stored on an external computer or within the fluorescent detector 200. Alternatively, the mathematical model may be hard wired circuitry either internal or external to the apparatus.

GFR and apparent volume of distribution can be measured by monitoring the plasma disappearance of the fluorescently labeled dextran molecule intravenously administered by a single dose bolus injection. FIG. 15 illustrates a widely used two-compartment model, also known as three-component model. The two compartments in question are vascular space and interstitial space. The basic assumption for this model is that the infused reporter molecule will distribute from the vascular space to interstitial space after the bolus injection, but the marker molecule will be retained in the vascular space. The plasma removal of the reporter molecule only occurs from the vascular space.

The plasma clearance rate and the inter-compartment clearance rate are denoted as G and k, respectively. The virtual volume for the vascular space and interstitial space are $V_1$ and $V_2$, respectively. As demonstrated by Sapirstein et al. (Sapirstein, L. A., D. G. Vidt, et al. (1955). "Volumes of distribution and clearances of intravenously injected creatinine in the dog." *American Journal of Physiology* 181(2): 330-6.) the amount change per unit time in $V_1$ is given by the following equation:

$$V_1 \frac{dC_1}{dt} = -GC_1 - k(C_1 - C_2) \quad (2)$$

Total injected amount D can be expressed as the following:

$$D = C_1 V_1 + C_2 V_2 + G\int_0^t C_1 dt \quad (3)$$

where $C_1$ and $C_2$ denote the concentrations of the reporter molecule in the vascular and interstitial space, respectively.

Combining the two equations above yields the following second order linear differential equation (Sapirstein, Vidt et al. 1955):

$$V_1 \frac{d^2 C_1}{dt^2} + \left( \frac{G+k}{V_1} + \frac{k}{V_2} \right) \frac{dC_1}{dt} + \frac{kGC_1}{V_1 V_2} = 0 \quad (4)$$

The general solution to equation (4) is a bi-exponential function expressed in equation (16) below:

$$C_1(t) = Ae^{-\alpha t} + Be^{-\beta t} \quad (5)$$

where the decay constants $\alpha$ and $\beta$ can be expressed in k, G, $V_1$ and $V_2$ (Sapirstein, L. A., D. G. Vidt, et al. (1955). "Volumes of distribution and clearances of intravenously injected creatinine in the dog." *American Journal of Physiology* 181(2): 330-6.).

Assuming the inter-compartment movement is negligible before the intra-compartment mixing in $V_1$ is completed, then the following two boundary conditions at t=0 become valid: $C_0 = D/V_1$ and $C_2 = 0$.

From equations (2), (3), (5), and the two boundary conditions we can derive the following (Sapirstein, L. A., D. G. Vidt, et al. (1955). "Volumes of distribution and clearances of intravenously injected creatinine in the dog." *American Journal of Physiology* 181(2): 330-6.):

$$GFR = \frac{D}{A/\alpha + B/\beta} \quad (6)$$

$$V_1 = \frac{D}{A+B} \quad (7)$$

$$V_d = \frac{D\left(\frac{A}{\alpha^2} + \frac{B}{\beta^2}\right)}{\left(\frac{A}{\alpha} + \frac{B}{\beta}\right)^2} \quad (8)$$

where the total extracellular volume of distribution $V_d$, is the sum of $V_1$ and $V_2$.

Parameters A, B, $\alpha$, and $\beta$ can be obtained by fitting the experimental data to equation (5).

In practice we may obtain $V_1$ using the marker molecule. If the linear relationship between the concentration and fluorescence intensity holds for the reporter molecule, equation (5) can then be rewritten as:

$$F_1(t) = A_1 e^{-\alpha t} + B_1 e^{-\beta t} \quad (9)$$

where $F_1$ is the fluorescence intensity of the reporter molecule as a function of time. $A_1$ and $B_1$ are constants.

Thus, equations (6) and (8) can be rewritten as follows:

$$GFR = \frac{V_1(A_1 + B_1)}{A_1/\alpha + B_1/\beta} \quad (10)$$

$$V_d = \frac{V_1(A_1 + B_1)\left(\frac{A_1}{\alpha^2} + \frac{B_1}{\beta^2}\right)}{\left(\frac{A_1}{\alpha} + \frac{B_1}{\beta}\right)^2} \quad (11)$$

where equation (10) represents GFR from intensity of a single, freely filterable reporter molecule type, and equation (11) represents the volume distribution associated with a single, freely filterable reporter molecule type.

In addition, since the fluorescence of the marker is a constant over time, equation (9) can be also expressed in terms of fluorescence ratio of the reporter molecule over the marker molecule. Thus, the bi-exponential equation becomes:

$$R(t) = A_2 e^{-\alpha t} + B_2 e^{-\beta t} \quad (12)$$

where R(t) is the fluorescence ratio of the reporter molecule over the marker molecule.

Constants $A_2$, $B_2$, $\alpha$, and $\beta$ can be obtained by fitting the experiment data to the above equation. Thus, the clearance GFR and the total volume of distribution can be expressed as:

$$GFR = \frac{V_1(A_2 + B_2)}{A_2/\alpha + B_2/\beta} \quad (13)$$

$$V_d = \frac{V_1(A_2 + B_2)\left(\frac{A_2}{\alpha^2} + \frac{B_2}{\beta^2}\right)}{\left(\frac{A_2}{\alpha} + \frac{B_2}{\beta}\right)^2} \quad (14)$$

where equation (13) represents GFR from the intensity ratio between a freely filterable reporter molecule type and a larger marker molecule type, and equation (11) represents the volume distribution associated with from a freely filterable reporter molecule type and a larger marker molecule type.

Evidently, when the inter-compartment volume exchange rate approaches zero, this model collapses to a single compartment model. However, it has been shown that as the plasma clearance level increases this mono-exponential approximation will lead to an overestimation of the GFR (Schwartz, G. J., S. Furth, et al. (2006). "Glomerular filtration rate via plasma iohexol disappearance: pilot study for chronic kidney disease in children." *Kidney International* 69(11): 2070-7; Yu, W., R. M. Sandoval, et al. (2007). "Rapid determination of renal filtration function using an optical ratiometric imaging approach." *American Journal of Physiology—Renal Physiology* 292(6): F1873-80.)

Optical Catheter

Figure 17:
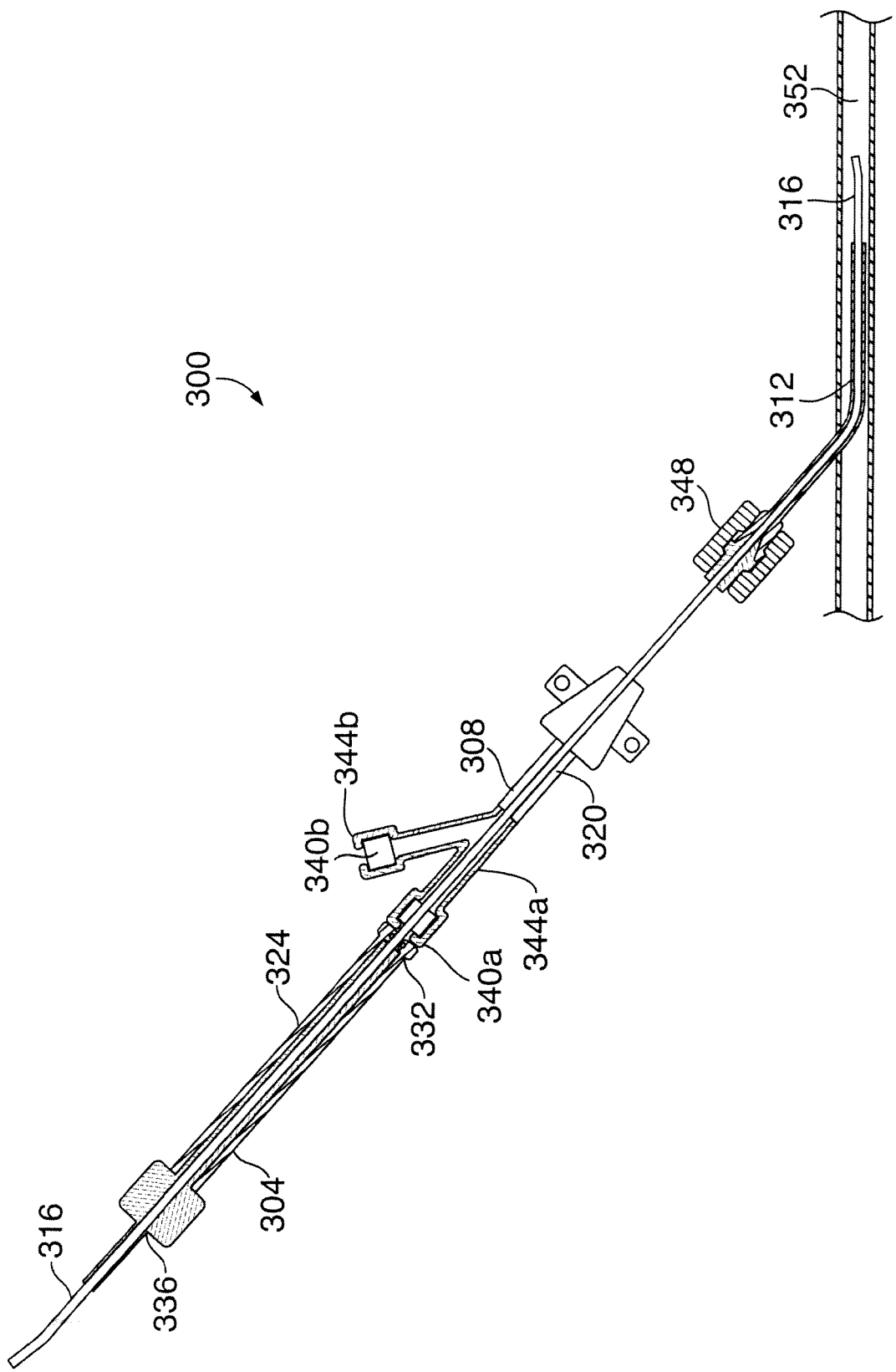
FIG. 17 is an illustration of the catheter of FIG. 16 assembled and inserted within a patient's vein.

Referring to FIGS. 16 and 17, the catheter 300 for use with the present invention is illustrated. The catheter 300 includes a fiber optic insertion tool 304, a dual port luman 308, and a French 5 to 8 size introducer 312. A standard 1 mm plastic fiber optical cable 316 may be inserted through a passageway 320 defined by a combination of the insertion tool 304 joined with the luman 308 joined with the introducer 312. Accordingly, each of these components is of a tubular configuration. Preferably, a 0.75 mm fiber optic cable is inserted through the passageway 320. The 0.75 mm diameter was only chosen to allow use of a standard 18 gauge introducer.

The insertion tool 304 includes a first tubular member 324 slidable within a second tubular member 328. Fluid-tight seals are provided on opposing ends of the second tubular member 328 by o-rings 332 about the first tubular member 324 and the fiber optic cable 316, respectively. The fiber optic cable 316 is securely held or fixed within the insertion tool 304 by a seal 336 at an opposite end of the insertion tool 304.

The insertion tool 304 is joined to one of the ports 340a on the luman 308. Homostatic seals 344a,b are located on the ports 340a,b. The other port 340b is to provide for bolus injection or a continuous infusion of the fluorescent molecule. A luer connector 348 at an opposite end of the luman 308 joins the subject with the introducer 312.

The fiber optic cable 316 may comprise either single or multiple single fibers for light delivery and collection of the emission and excitation. The fiber optic cable 316 is inserted within a subject's vein 352 by pressing the first tubular member 324 and the captive optical cable 316 through the second tubular member 328 wherein the fiber optic cable 316 is extensible from the catheter 300. The optical cable 316 traverses through the subject by the luer connector 348 through the introducer 312 and into the subject's vein 352. The fiber optic cable 316 may have a small permanent bend on an end inserted into the subject's vein 352. This bend helps penetrate the tissue and minimizes interference of the fiber optic cable 316 within the vein.

In use, the fiber optic cable 316 is an extension of, or placed in communication with, the fiber optic cable 210 of the fluorescent detector 200 to transmit a signal or signals generated at the subject's vein to the fluorescent detector 200 for evaluation.

The present invention discloses a unique and novel method and device for quantifying kidney function, but it also presents a unique method of quantitatively determining liver function. For example, a dye composition of a larger molecular weight marker and smaller molecular weight reporter molecules is injected into a subject, and the ratio of the decrease of the reporter molecule to the marker molecule is used to detect kidney function. The smaller reporter molecules are filtered by the kidney while the marker molecules are remained in the vascular system. For a reasonable ratio of marker molecules to signal molecules to be detected, the marker molecule must remain in the blood at relatively consistent levels during the diagnostic test. Eventually on a much longer time scale (typically 12 to 24 hours) the marker molecule will typically be absorbed and processed from the vascular system by the liver instead of the kidney. Here a novel method and device are described, where relative liver function and health may be quantitatively determined by measuring the absolute decrease of the marker molecule in the blood over time. This method will have advantages over other methods by providing a quantitative value on an arbitrary scale that correlates to liver health. As a result, medical care professionals will be provided with a new tool allowing them to better treat their patients and predict proper dosing of certain drugs. This method would use the same device as described previously, and would also utilize the same dye composition as described previously; however, it would provide a method of analyzing the results to provide additional function and utility using the following equation:

$$LiverFunction = \frac{\text{Emission from Marker Molecule}}{\text{time}} \quad (15)$$

While the specific embodiments have been illustrated and described, numerous modifications come to mind without significantly departing from the spirit of the invention, and the scope of protection is only limited by the scope of the accompanying Claims.

What is claimed is:

1. A method for measuring glomerular filtration rate in a kidney of a mammalian subject, the method comprising:
   providing a fluid comprising a plurality of fluorescent reporter molecules and a plurality of fluorescent marker molecules in a predetermined ratio, wherein the plurality of reporter molecules have lower molecular weights than the molecular weights of the plurality of marker molecules, the plurality of marker molecules having a glomerular sieving coefficient (GSC) of 0.0;
   introducing the fluid into a vascular space of the mammalian subject;

exciting at least one of the plurality of reporter molecules with a first fluorescence excitation wavelength to generate a first fluorescence emission signal having a first fluorescence emission wavelength and exciting at least one of the plurality of marker molecules with a second fluorescence excitation wavelength to generate a second fluorescence emission signal having a second fluorescence emission wavelength within the vascular space;

measuring an intensity of the first fluorescence emission signal and the intensity of the second fluorescence emission signal;

determining a ratio of intensity of the first fluorescence emission signal to the intensity of the second fluorescence emission signal in a real time;

$$R(t) = A_2 e^{-\alpha t} + B_2 e^{-\beta t}$$

determining $A_2$, $B_2$, $\alpha$, and $\beta$ by curve fitting to the above equation in real time, where $R(t)$ is a function of time and defines the fluorescence emission ratio of the at least one of the plurality of reporter molecule over the at least one of the plurality of marker molecule, where $A_2$ and $B_2$ are constants; $\alpha$ is a fast phase decay constant; and $\beta$ is a slow phase decay constant; and calculating the glomerular filtration rate of the kidney according to the equation:

$$GFR = \frac{V_1(A_2 + B_2)}{A_2/\alpha + B_2/\beta}$$

wherein $V_1$ is a virtual volume for the vascular space.

2. The method of claim 1 further comprising, wherein a volume distribution associated with said reporter molecule, said volume distribution calculated according to equation:

$$V_d = \frac{V_1(A_2 + B_2)\left(\frac{A_2}{\alpha^2} + \frac{B_2}{\beta^2}\right)}{\left(\frac{A_2}{\alpha} + \frac{B_2}{\beta}\right)^2}$$

wherein $V_d$ is total extracellular volume of distribution, $V_1$ is the virtual volume of a vascular space, said constants $A_2$ and $B_2$ are constants, and $\alpha$ are defined as above.

3. The method of claim 1, wherein said plurality of reporter molecules are filtered by the kidney, and said plurality of marker molecules are retained in the vascular space.

4. The method of claim 1, wherein said plurality of reporter molecules and said plurality of marker molecules are chemically stable in the vascular space during measurement of the kidney function.

5. The method of claim 1, wherein said plurality of reporter molecules and said plurality of marker molecules are fluoresceins.

6. The method of claim 1, wherein said plurality of reporter molecules and said plurality of marker molecules comprise dextrans.

7. The method of claim 1, wherein said plurality of marker molecules have a greater molecular weight than said plurality of reporter molecules.

8. The method of claim 1, wherein said plurality of reporter molecules have a molecular weight between 3 kDa and 70 kDa.

9. The method of claim 1, wherein said plurality of marker molecules have a molecular weight ranging between 100-500 kDa.

10. The method of claim 1, wherein said plurality of reporter molecules have a first fluorescent characteristic and said plurality of marker molecules have a second fluorescent characteristic, and wherein said first fluorescent characteristic and said second fluorescent characteristic are distinguishable.

11. The method of claim 10, wherein said first fluorescent characteristic is a first excitation wavelength and a first emission wavelength and said second fluorescent characteristic is a second excitation wavelength and a second emission wavelength, said first and second fluorescence excitation wavelengths and said first and second fluorescence emission wavelengths being unequal.

12. The method of claim 1, wherein the step of introducing is performed by introducing a catheter into said vascular space.

13. The method of claim 1, wherein said step of measuring is performed using an optic fiber in communication with a detector.

14. The method of claim 1 wherein said measuring and calculating steps are performed at predetermined intervals and reported in at least substantially real time.

15. The method of claim 1, wherein the step of introducing is performed by a bolus injection.

16. The method of claim 1, wherein said ratio of fluorescence intensities is examined from an image within blood vessel regions of said vascular space.

17. The method of claim 1, wherein the plurality of reporter molecules have molecular weights between 3 kD and 20 kD.

18. The method of claim 1, wherein the plurality of marker molecules have molecular weights greater than about 100 kD.

* * * * *